(12) United States Patent
Liu et al.

(10) Patent No.: US 7,795,179 B2
(45) Date of Patent: Sep. 14, 2010

(54) SUBSTITUTED AZOLE COMPOUNDS AND ITS PREPARATION AND USE THEREOF

(75) Inventors: Changling Liu, Shenyang (CN); Miao Li, Shenyang (CN); Hong Zhang, Shenyang (CN); Lin Li, Shenyang (CN); Mingxing Zhang, Shenyang (CN); Aiying Guan, Shenyang (CN); Chunqing Hou, Shenyang (CN); Zhinian Li, Shenyang (CN); Yonggang Jia, Shenyang (CN)

(73) Assignee: Shenyang Research Institute of Chemical Industry, Shenyang (CN)

( * ) Notice: Subject to any disclaimer, the term of this patent is extended or adjusted under 35 U.S.C. 154(b) by 265 days.

(21) Appl. No.: 10/598,033

(22) PCT Filed: Feb. 17, 2005

(86) PCT No.: PCT/CN2005/000195

§ 371 (c)(1), (2), (4) Date: Aug. 16, 2006

(87) PCT Pub. No.: WO2005/080344

PCT Pub. Date: Sep. 1, 2005

(65) Prior Publication Data

US 2008/0108668 A1 May 8, 2008

(30) Foreign Application Priority Data

Feb. 20, 2004 (CN) .................. 2004 1 0021172

(51) Int. Cl.
A01N 43/56 (2006.01)
C07D 231/54 (2006.01)
C07D 487/00 (2006.01)
C07D 487/02 (2006.01)

(52) U.S. Cl. .................. 504/281; 504/282; 548/358.1

(58) Field of Classification Search .................. 504/281, 504/282; 514/358.1
See application file for complete search history.

(56) References Cited

U.S. PATENT DOCUMENTS

| | | | |
|---|---|---|---|
| 5,185,342 A | 2/1993 | Hayase et al. | |
| 5,221,691 A | 6/1993 | Clough et al. | |
| 5,342,837 A | 8/1994 | Clough et al. | |
| 5,935,986 A | 8/1999 | Muller et al. | |
| 6,031,110 A * | 2/2000 | Kirstgen et al. | 548/370.1 |
| 6,054,592 A | 4/2000 | Muller et al. | |
| 6,075,149 A | 6/2000 | Kirstgen et al. | |
| 6,274,586 B1 | 8/2001 | Bayer et al. | |
| 6,562,856 B1 | 5/2003 | Heinemann et al. | |
| 6,589,974 B1 | 7/2003 | Heinemann et al. | |
| 6,605,631 B1 | 8/2003 | Kirstgen et al. | |

FOREIGN PATENT DOCUMENTS

| | | |
|---|---|---|
| CN | 1065658 | 10/1992 |
| CN | 1118165 | 3/1996 |
| CN | 1154692 | 7/1997 |
| CN | 1175575 | 3/1998 |
| CN | 200410021172.3 | * 4/2005 |
| WO | WO 99/33812 | * 7/1999 |

OTHER PUBLICATIONS

Frank D. King, "Bioisosteres, Conformational Restriction, and Prodrugs—Case History: An Example of a Conformational Restriction Approach," Medicinal Chemistry: Principles and Practice, Chapter 14, 1994, pp. 206-225.*
International Search Report for PCT/CN2005/000195.

* cited by examiner

*Primary Examiner*—San-ming Hui
*Assistant Examiner*—Paul Zarek
(74) *Attorney, Agent, or Firm*—Smith, Gambrell & Russell, LLP

(57) ABSTRACT

The invention relates to fungicide and insecticide, especifically to the substituted azole compounds and its preparation method and use thereof. The azole compounds of the invention having general formula (I):

The compounds of present invention, having broad spectrum fungicidal activity, applied for controlling various disease in plants. For example they have good activity against the diseases such as cucumber downy mildew, cucumber grey mold, cucumber powdery mildew, tomato early blight, tomato late blight, phytophthora blight of pepper, grape downy mildew, grape white rot, apple ring rot, apple alternaria leaf spot, rice sheath blight, rice blast, wheat leaf rust, wheat leaf blotch, wheat powdery mildew, rapesclerotiniose, corn southern leaf blight. Some compounds have good insecticidal or acaricidal activity and can be used to control insects and acacids of various crops. For example they are used to control army worm, diamond backmoth and aphid, and culex mosquito.

13 Claims, No Drawings

SUBSTITUTED AZOLE COMPOUNDS AND ITS PREPARATION AND USE THEREOF

This application is a 371 application of PCT/CN05/00195, filed 17 Feb. 2005 and claims the benefit of Chinese Patent Application Ser. No. 200410021172.3, filed 20 Feb. 2004.

FIELD OF THE INVENTION

The invention relates to fungicide or insecticide, especifically to substituted azole compounds and its preparation method and use thereof

BACKGROUND OF THE INVENTION

Strobilurin (methoxyacrylate) compounds are natural products and known with biological active. Fungicide pyraclostrobin with broad spectrum was disclosed in U.S. Pat. No. 5,869,517, U.S. Pat. No. 6,054,592, CN1154692A and CN1308065A. The structure of pyraclostrobin is as follows:

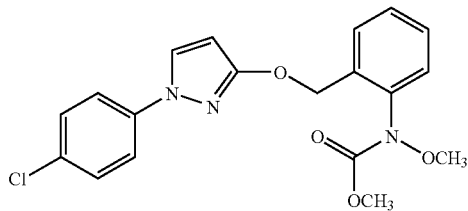

The following Compound with fungicidal activity was also disclosed in DE19548786:

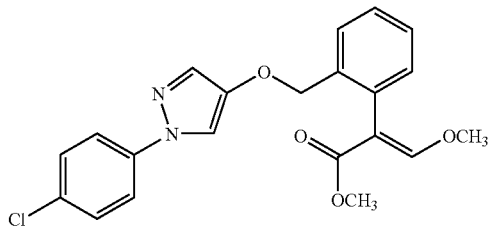

The following Compound with fungicidal activity is known in patent WO9933812:

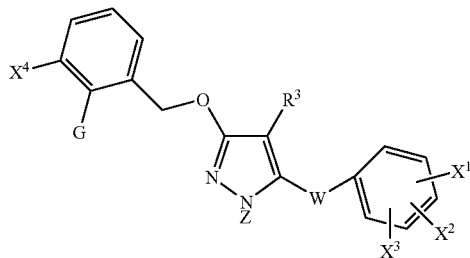

The above compounds were similar to this invention, but there are some obvious difference.

SUMMARY OF THE INVENTION

The aim of the present invention is to provide substituted azole compounds with biological activity against all sorts of plant disease and insects at very low dosage, and the compounds can be applied in agriculture to control disease and insects in plant.

Detailed description of the invention is as follows:
The present invention offered substituted azole compounds having general formula (I):

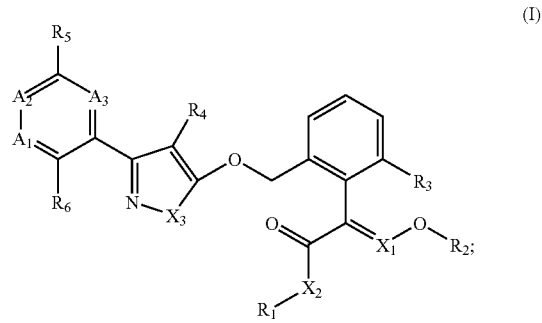

wherein: $X_1$ is selected from CH or N; $X_2$ is selected from O, S or $NR_7$; $X_3$ is selected from O, S or $NR_8$;

$A_1$ is selected from N or $CR_9$; $A_2$ is selected from N or $CR_{10}$; $A_3$ is selected from N or $CR_{11}$; and if selected from N, only one of $A_1$, $A_2$ or $A_3$ is selected from N.

$R_1$, $R_2$ may be the same or different, selected from H, $C_1$-$C_{12}$ alkyl or $C_1$-$C_{12}$ haloalkyl;

$R_3$ is selected from H, halo, $C_1$-$C_{12}$alkyl, $C_1$-$C_{12}$haloalkyl or $C_1$-$C_{12}$alkoxy;

$R_7$ is selected from H or $C_1$-$C_{12}$alkyl;

$R_8$ is selected from H, $C_1$-$C_{12}$alkyl; $C_1$-$C_{12}$haloalkyl; $C_1$-$C_{12}$alkoxycarbonyl or $C_1$-$C_{12}$alkoxycarbonyl$C_1$-$C_{12}$alkyl;

$R_4$, $R_5$, $R_6$, $R_9$, $R_{10}$ and $R_{11}$, may be the same or different, selected from H, halo, $NO_2$, CN, $CONH_2$, $CH_2CONH_2$, $CH_2CN$, $C_1$-$C_{12}$alkyl, $C_1$-$C_{12}$haloalkyl, $C_1$-$C_{12}$alkoxy, $C_1$-$C_{12}$haloalkoxy, $C_1$-$C_{12}$alkylthio, $C_1$-$C_{12}$alkylsulfonyl, $C_1$-$C_2$alkylcarbonyl, $C_1$-$C_{12}$alkoxy$C_1$-$C_{12}$alkyl, $C_1$-$C_{12}$alkoxycarbonyl, $C_1$-$C_{12}$alkoxycarbonyl$C_1$-$C_{12}$alkyl, $C_1$-$C_{12}$haloalkoxy$C_1$-$C_{12}$alkyl, or groups may be substituted by any other groups: amino$C_1$-$C_{12}$alkyl, aryl, heteroaryl; aroxyl, aryl$C_1$-$C_{12}$alkyl, aryl$C_1$-$C_{12}$alkoxy, heteroaryl$C_1$-$C_{12}$alkyl or heteroaryl$C_1$-$C_{12}$alkoxy; and stereoisomer.

The preferred compounds of general formula (I) of this invention are:

$X_1$ is selected from CH or N; $X_2$ is selected from O, S or $NR_7$; $X_3$ is selected from O, S or $NR_8$;

$A_1$ is selected from N or $CR_9$, $A_2$ is selected from N or $CR_{10}$, $A_3$ is selected from N or $CR_{11}$, and if selected from N, only one of $A_1$, $A_2$ or $A_3$ is selected from N;

$R_1$, $R_2$ may be the same or different, select from H, $C_1$-$C_6$alkyl or $C_1$-$C_6$haloalkyl;

$R_3$ is selected from H, halo, $C_1$-$C_6$alkyl, $C_1$-$C_6$haloalkyl or $C_1$-$C_6$alkoxy;

$R_7$ is selected from H or $C_1$-$C_6$alkyl;

$R_8$ is selected from H, $C_1$-$C_6$alkyl; $C_1$-$C_6$haloalkyl; $C_1$-$C_6$alkoxycarbonyl or $C_1$-$C_6$alkoxycarbonyl$C_1$-$C_6$alkyl;

$R_4$, $R_5$, $R_6$, $R_9$, $R_{10}$ and $R_{11}$, may be the same or different, selected from H, halo, $NO_2$, CN, $CONH_2$, $CH_2CONH_2$, $CH_2CN$, $C_1$-$C_6$alkyl, $C_1$-$C_6$haloalkyl, $C_1$-$C_6$alkoxy, $C_1$-$C_6$haloalkoxy, $C_1$-$C_6$alkylthio, $C_1$-$C_6$alkylsulfonyl, $C_1$-$C_6$alkylcarbonyl, $C_1$-$C_6$alkoxy$C_1$-$C_6$alkyl, $C_1$-$C_6$alkoxycarbonyl, $C_1$-$C_6$alkoxycarbonyl$C_1$-$C_6$alkyl, $C_1$-$C_6$haloalkoxy$C_1$-$C_6$alkyl, or groups may be substituted by any other groups: amino$C_1$-$C_6$alkyl, aryl, heteroaryl, aroxyl, aryl$C_1$-$C_6$alkyl, aryl$C_1$-$C_6$alkoxy, heteroaryl$C_1$-$C_6$alkyl or heteroaryl$C_1$-$C_6$alkoxy.

Furthermore, the preferred compounds of general formula (I) of this invention are:

$X_1$ is selected from CH or N; $X_2$ is selected from O or NH; $X_3$ is selected from O, S or $NR_8$;

$A_1$ is selected from N or $CR_9$, $A_2$ is selected from N or $CR_{10}$, $A_3$ is selected from N or $CR_{11}$, and if selected from N, only one of $A_1$, $A_2$ or $A_3$ is selected from N;

$R_1$, $R_2$ is $CH_3$;

$R_3$ is selected from H or $CH_3$;

$R_8$ is selected from H, $C_1$-$C_6$alkyl, $C_1$-$C_6$haloalkyl, $C_1$-$C_3$alkoxycarbonyl or $C_1$-$C_6$alkoxycarbonyl$C_1$-$C_3$alkyl;

$R_4$, $R_5$, $R_6$, $R_9$, $R_{10}$ and $R_{11}$, may be the same or different, selected from H, halo, $NO_2$, CN, $CONH_2$, $CH_2CONH_2$, $CH_2CN$, $C_1$-$C_6$alkyl, $C_1$-$C_6$haloalkyl, $C_1$-$C_6$alkoxy, $C_1$-$C_6$haloalkoxy, $C_1$-$C_6$alkylthio, $C_1$-$C_6$alkylsulfonyl, $C_1$-$C_6$alkylcarbonyl, $C_1$-$C_6$alkoxy$C_1$-$C_6$alkyl, $C_1$-$C_6$alkoxycarbonyl, $C_1$-$C_6$alkoxycarbonylC i -$C_6$alkyl, $C_1$-$C_6$haloalkoxy$C_1$-$C_6$alkyl, or groups may be substituted by any other groups: amino$C_1$-$C_3$alkyl, phenyl, phenoxy, benzyl or benzyloxy.

Even more preferred compounds of formula (I) of this invention are:

$X_1$ is selected from CH or N; $X_2$ is selected from O or NH; $X_3$ is selected from O or $NR_8$;

$A_1$ is selected from N or $CR_9$, $A_2$ is selected from N or $CR_{10}$, $A_3$ is selected from N or $CR_{11}$, and if selected from N, only one of $A_1$, $A_2$ or $A_3$ is selected from N;

R1, R2 is $CH_3$;

$R_3$ is H;

$R_8$ is selected from H, $C_1$-$C_3$alkyl; $C_1$-$C_3$haloalkyl; $C_1$-$C_3$alkoxycarbonyl or $C_1$-$C_3$alkoxycarbonyl$C_1$-$C_3$alkyl;

$R_4$, $R_5$, $R_6$, $R_9$, $R_{10}$ and $R_{11}$ may be the same or different, selected from H, Cl, Br, F, $NO_2$, CN, $CH_2CN$, $C_1$-$C_6$alkyl, $C_1$-$C_6$haloalkyl, $C_1$-$C_6$alkoxy, $C_1$-$C_6$haloalkoxy, $C_1$-$C_6$alkylthio, $C_1$-$C_6$alkylsulfonyl, $C_1$-$C_6$alkylcarbonyl, $C_1$-$C_6$alkoxycarbonyl, $C_1$-$C_6$alkoxycarbonyl$C_1$-$C_6$alkyl, $C_1$-$C_6$alkoxy$C_1$-$C_3$alkyl, $C_1$-$C_3$haloalkoxy$C_1$-$C_3$alkyl, substituted amino$C_1$-$C_3$alkyl, phenyl or substituted phenyl, phenoxy or substituted phenoxy.

Most preferred compounds of formula (I) of this invention are:

$X_1$ is selected from CH or N; $X_2$ is selected from O or NH; $X_3$ is selected from O or $NR_8$;

$A_1$ is selected from N or $CR_9$, $A_2$ is selected from N or $CR_{10}$, $A_3$ is selected from N or $CR_{11}$, and if selected from N, only one of $A_1$, $A_2$ or $A_3$ is selected from N;

R1, R2 is $CH_3$;

$R_3$ is H;

$R_8$ is selected from H, $C_1$-$C_3$alkyl; $C_1$-$C_3$haloalkyl; $C_1$-$C_3$alkoxycarbonyl or $C_1$-$C_3$alkoxycarbonyl$C_1$-$C_3$alkyl;

$R_4$, $R_5$, $R_6$, $R_9$, $R_{10}$ and $R_{11}$, may be the same or different, selected from H, Cl, Br, F, $NO_2$, CN, $C_1$-$C_6$alkyl, $C_1$-$C_6$haloalkyl, $C_1$-$C_6$alkoxy, $C_1$-$C_6$haloalkoxy, $C_1$-$C_6$alkylthio, $C_1$-$C_6$alkylsulfonyl, $C_1$-$C_6$alkylcarbonyl, $C_1$-$C_6$alkoxycarbonyl, $C_1$-$C_6$alkoxycarbonyl$C_1$-$C_6$alkyl, $C_1$-$C_6$alkoxy$C_1$-$C_3$alkyl, phenyl or halo phenyl, phenoxy or halophenoxy.

The following is the meaning of terms in the general formula (I):

Phenoxy, benzyloxy, phenyl, benzyl may be substituted at any position by 0-5 groups, selected from H, alkyl, alkoxy, haloalkyl, haloalkoxy, halo, $NO_2$ or CN etc.

Halogen or halo is meant to include fluoro, chloro, bromo and iodo.

The alkyl includes either straight or branched chain alkyl such as methyl, ethyl, propyl, isopropyl and tert-butyl.

The haloalkyl refers to straight or branched chain alkyl, in which hydrogen atom may be all or partly substituted with halogen, such as chloromethyl, dichloromethyl, trichloromethyl, fluoromethyl, difluoromethyl, trifluoromethyl.

The alkoxy refers to straight or branched chain alkyl, which is linked to the structure by oxygen atom.

The haloalkoxy refers to straight or branched chain alkoxy, in which hydrogen atom may be all or partly substituted with halogen, such as chloromethoxy, dichloromethoxy, trichloromethoxy, fluoromethoxy, difluoromethoxy, trifluoromethoxy, chlorofluoromethoxy or trifluoroethoxy The alkenyl refers to a straight or branched, having double bonds at any position such as vinyl or allyl. Substituted alkenyl includes arylvinyl which is substituted at any position with any group.

The alkynyl refers to a straight or branched, having triple bonds at any position. Such as ethynyl, propynyl. Substituted alkynyl includes arylethynyl which is substituted at any position with any group.

The aryl and aryl in arylalkyl, arylalkenyl, arylalkynyl, aryloxy, aryloxyalkyl include phenyl and naphthyl.

The hetero aryl in this invention refers to five member ring or six member ring containing one or many N, O, S hetero atom. Such as pyridine, furan, pyrimidine, pyrazine, pyridazine, triazine, quinoline or benzofuran.

Because of the C=C or C=N link to different substituted group, the compounds of the invention may form geometrical isomer (the different isomers are respectively expressed with Z and E). Z isomer and E isomer and their mixture in any proportion are included in the invention.

The present invention is explained by the following compounds in table 1-3, but without being restricted thereby.

TABLE 1

(I)

wherein: $R_1$, $R_2$ = $CH_3$, $R_3$ = H, $X_1$ = CH, $X_2$ = O

| No. | $X_3$ | $R_4$ | $R_5$ | $R_6$ | $A_1$ | $A_2$ | $A_3$ |
|---|---|---|---|---|---|---|---|
| 1 | $NCH_3$ | H | H | H | CH | CH | CH |
| 2 | $NCH_3$ | H | H | H | CH | C—Cl | CH |

TABLE 1-continued (I)

wherein: $R_1, R_2 = CH_3, R_3 = H, X_1 = CH, X_2 = O$

| No. | $X_3$ | $R_4$ | $R_5$ | $R_6$ | $A_1$ | $A_2$ | $A_3$ |
|---|---|---|---|---|---|---|---|
| 3 | $NCH_3$ | H | H | H | CH | C—F | CH |
| 4 | $NCH_3$ | H | H | H | CH | C—$NO_2$ | CH |
| 5 | $NCH_3$ | H | H | H | CH | C—$CF_3$ | CH |
| 6 | $NCH_3$ | H | H | H | CH | C—CN | CH |
| 7 | $NCH_3$ | H | H | H | CH | C—$CH_3$ | CH |
| 8 | $NCH_3$ | H | H | H | CH | C—$OCH_3$ | CH |
| 9 | $NCH_3$ | H | H | H | CH | C—$OCF_3$ | CH |
| 10 | $NCH_3$ | H | H | H | CH | C—Cl | C—Cl |
| 11 | $NCH_3$ | H | H | H | C—F | C—Cl | C—Cl |
| 12 | $NCH_3$ | H | H | H | C—$OCH_3$ | C—$OCH_3$ | CH |
| 13 | $NCH_3$ | H | H | H | CH | C—F | C—Cl |
| 14 | $NCH_3$ | H | Cl | H | C—Cl | CH | CH |
| 15 | $NCH_3$ | H | H | H | CH | C—$CH_3$ | CH |
| 16 | $NCH_3$ | Cl | H | H | CH | CH | CH |
| 17 | $NCH_3$ | Cl | H | H | CH | C—Cl | CH |
| 18 | $NCH_3$ | Cl | H | H | CH | C—F | CH |
| 19 | $NCH_3$ | Cl | H | H | CH | C—$NO_2$ | CH |
| 20 | $NCH_3$ | Cl | H | H | CH | C—$CF_3$ | CH |
| 21 | $NCH_3$ | Cl | H | H | CH | C—CN | CH |
| 22 | $NCH_3$ | Cl | H | H | CH | C—$CO_2Me$ | CH |
| 23 | $NCH_3$ | Cl | H | H | CH | C—$OCH_3$ | CH |
| 24 | $NCH_3$ | Cl | H | H | CH | C—$OCF_3$ | CH |
| 25 | $NCH_3$ | Cl | H | H | CH | C—Cl | C—Cl |
| 26 | $NCH_3$ | Cl | H | H | C—F | C—Cl | C—Cl |
| 27 | $NCH_3$ | Cl | H | H | CH | C—F | C—Cl |
| 28 | $NCH_3$ | Cl | Cl | H | C—Cl | CH | CH |
| 29 | $NCH_3$ | CN | H | H | CH | C—Cl | CH |
| 30 | $NCH_3$ | $CH_3$ | H | H | CH | C—Cl | CH |
| 31 | $NCH_3$ | CN | H | H | CH | C—F | CH |
| 32 | $NCH_3$ | CN | H | H | CH | C—$NO_2$ | CH |
| 33 | $NCH_3$ | CN | H | H | CH | C—$CF_3$ | CH |
| 34 | $NCH_3$ | CN | H | H | CH | C—CN | CH |
| 35 | $NCH_3$ | $OCH_3$ | H | H | CH | C—$CO_2Me$ | CH |
| 36 | $NCH_3$ | CN | H | H | CH | C—$OCH_3$ | CH |
| 37 | $NCH_3$ | CN | H | H | CH | C—$OCF_3$ | CH |
| 38 | $NCH_3$ | CN | H | H | CH | C—Cl | C—Cl |
| 39 | $NCH_3$ | CN | H | H | C—F | C—Cl | C—Cl |
| 40 | $NCH_3$ | CN | H | H | C—$OCH_3$ | C—$OCH_3$ | CH |
| 41 | $NCH_3$ | $OCH_3$ | H | H | CH | C—F | C—Cl |
| 42 | $NCH_3$ | Br | H | H | CH | C—Cl | CH |
| 43 | $NCH_3$ | $CO_2Me$ | H | H | CH | CH | CH |
| 44 | $NCH_3$ | $CO_2Me$ | H | H | CH | C—Cl | CH |
| 45 | $NCH_3$ | $CO_2Me$ | H | H | CH | C—F | CH |
| 46 | $NCH_3$ | $CO_2Me$ | H | H | CH | C—$NO_2$ | CH |
| 47 | $NCH_3$ | $CO_2Me$ | H | H | CH | C—$CF_3$ | CH |
| 48 | $NCH_3$ | $CO_2Me$ | H | H | CH | C—CN | CH |
| 49 | $NCH_3$ | $CO_2Me$ | H | H | CH | C—$CO_2Me$ | CH |
| 50 | $NCH_3$ | $CO_2Me$ | H | H | CH | C—$OCH_3$ | CH |
| 51 | $NCH_3$ | $CO_2Me$ | H | H | CH | C—$OCF_3$ | CH |
| 52 | $NCH_3$ | $CO_2Me$ | H | H | CH | C—Cl | C—Cl |
| 53 | $NCH_3$ | $CO_2Me$ | H | H | C—F | C—Cl | C—Cl |
| 54 | $NCH_3$ | $CO_2Me$ | H | H | C—$OCH_3$ | C—$OCH_3$ | CH |
| 55 | $NCH_3$ | $CO_2Me$ | H | H | CH | C—F | C—Cl |
| 56 | $NCH_3$ | $CO_2Me$ | Cl | H | C—Cl | CH | CH |
| 57 | $NCH_3$ | H | H | H | CH | CH | N |
| 58 | $NCH_3$ | H | H | H | CH | C—Cl | N |
| 59 | $NCH_3$ | H | H | H | CH | C—$OCH_3$ | N |
| 60 | $NCH_3$ | H | H | H | C—Cl | CH | N |
| 61 | $NCH_3$ | H | H | H | CH | C—$CF_3$ | N |

TABLE 1-continued

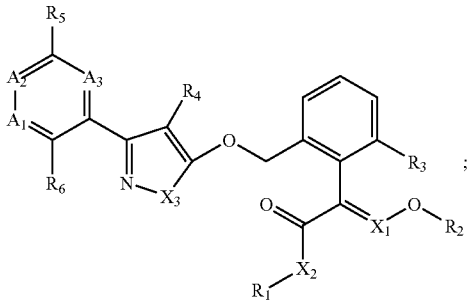

(I)

wherein: $R_1, R_2 = CH_3, R_3 = H, X_1 = CH, X_2 = O$

| No. | $X_3$ | $R_4$ | $R_5$ | $R_6$ | $A_1$ | $A_2$ | $A_3$ |
|---|---|---|---|---|---|---|---|
| 62 | $NCH_3$ | H | H | Cl | CH | $C-CF_3$ | N |
| 63 | $NCH_3$ | Cl | H | H | CH | CH | N |
| 64 | $NCH_3$ | Cl | H | H | CH | $C-Cl$ | N |
| 65 | $NCH_3$ | Cl | H | H | CH | $C-OCH_3$ | N |
| 66 | $NCH_3$ | Cl | H | H | $C-Cl$ | CH | N |
| 67 | $NCH_3$ | Cl | H | H | CH | $C-CF_3$ | N |
| 68 | $NCH_3$ | Cl | H | Cl | CH | $C-CF_3$ | N |
| 69 | $NCH_3$ | H | H | H | N | $C-Cl$ | CH |
| 70 | $NCH_3$ | H | H | H | N | $C-F$ | CH |
| 71 | $NCH_3$ | H | H | H | N | $C-OCF_3$ | CH |
| 72 | $NCH_3$ | H | H | H | N | $C-CF_3$ | CH |
| 73 | $NCH_3$ | H | H | H | N | $C-OCH_3$ | CH |
| 74 | $NCH_3$ | H | H | H | CH | $C-OCH_2CF_3$ | CH |
| 75 | $NCH_3$ | H | H | H | N | $C-CF_3$ | $C-Cl$ |
| 76 | $NCH_3$ | Cl | H | H | N | $C-F$ | CH |
| 77 | $NCH_3$ | Cl | H | H | N | $C-OCF_3$ | CH |
| 78 | $NCH_3$ | Cl | H | H | N | $C-CF_3$ | CH |
| 79 | $NCH_3$ | Cl | H | H | N | $C-OCH_3$ | CH |
| 80 | $NCH_3$ | Cl | H | H | N | $C-OCH_2CF_3$ | CH |
| 81 | $NCH_3$ | H | H | H | CH | N | CH |
| 82 | $NCH_3$ | Cl | H | H | CH | N | CH |
| 83 | O | H | H | H | CH | CH | CH |
| 84 | O | H | H | H | CH | $C-Cl$ | CH |
| 85 | O | H | H | H | CH | $C-F$ | CH |
| 86 | O | H | H | H | CH | $C-NO_2$ | CH |
| 87 | O | H | H | H | CH | $C-CF_3$ | CH |
| 88 | O | H | H | H | CH | $C-CN$ | CH |
| 89 | O | H | H | H | CH | $C-CO_2Me$ | CH |
| 90 | O | H | H | H | CH | $C-OCH_3$ | CH |
| 91 | O | H | H | H | CH | $C-OCF_3$ | CH |
| 92 | O | H | H | H | CH | $C-Cl$ | $C-Cl$ |
| 93 | O | H | H | H | $C-F$ | $C-Cl$ | $C-Cl$ |
| 94 | O | H | H | H | $C-OCH_3$ | $C-OCH_3$ | CH |
| 95 | O | H | H | H | CH | $C-F$ | $C-Cl$ |
| 96 | O | H | Cl | H | $C-Cl$ | CH | CH |
| 97 | O | H | H | H | CH | $C-CH_3$ | CH |
| 98 | O | Cl | H | H | CH | $C-Cl$ | CH |
| 99 | O | Cl | H | H | CH | $C-F$ | CH |
| 100 | O | Cl | H | H | CH | $C-NO_2$ | CH |
| 101 | O | Cl | H | H | CH | $C-CF_3$ | CH |
| 102 | O | Cl | H | H | CH | $C-CN$ | CH |
| 103 | O | Cl | H | H | CH | $C-CO_2Me$ | CH |
| 104 | O | Cl | H | H | CH | $C-OCH_3$ | CH |
| 105 | O | Cl | H | H | CH | $C-OCF_3$ | CH |
| 106 | O | Cl | H | H | CH | $C-Cl$ | $C-Cl$ |
| 107 | O | Cl | H | H | $C-F$ | $C-Cl$ | $C-Cl$ |
| 108 | O | Cl | H | H | $C-OCH_3$ | $C-OCH_3$ | CH |
| 109 | O | Cl | H | H | CH | $C-F$ | $C-Cl$ |
| 110 | O | Cl | Cl | H | $C-Cl$ | CH | CH |
| 111 | O | $CH_3$ | H | H | CH | $C-Cl$ | CH |
| 112 | O | $CH_3$ | H | H | CH | $C-OCH_2CF_3$ | CH |
| 113 | O | CN | H | H | CH | $C-F$ | CH |
| 114 | O | CN | H | H | CH | $C-NO_2$ | CH |
| 115 | O | CN | H | H | CH | $C-CF_3$ | CH |
| 116 | O | CN | H | H | CH | $C-CN$ | CH |
| 117 | O | CN | H | H | CH | $C-CO_2Me$ | CH |
| 118 | O | CN | H | H | CH | $C-OCH_3$ | CH |
| 119 | O | CN | H | H | CH | $C-OCF_3$ | CH |
| 120 | O | CN | H | H | CH | $C-Cl$ | $C-Cl$ |

TABLE 1-continued

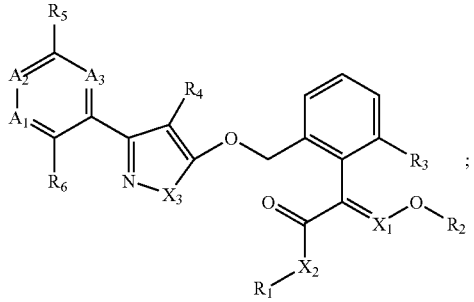

(I)

wherein: $R_1$, $R_2$ = $CH_3$, $R_3$ = H, $X_1$ = CH, $X_2$ = O

| No. | $X_3$ | $R_4$ | $R_5$ | $R_6$ | $A_1$ | $A_2$ | $A_3$ |
|---|---|---|---|---|---|---|---|
| 121 | O | CN | H | H | C—F | C—Cl | C—Cl |
| 122 | O | $OCH_3$ | H | H | CH | C—Cl | CH |
| 123 | O | $OCH_3$ | H | H | CH | C—F | CH |
| 124 | O | $OCH_3$ | H | H | CH | C—$CF_3$ | CH |
| 125 | O | $CO_2Me$ | H | H | CH | CH | CH |
| 126 | O | $CO_2Me$ | H | H | CH | C—Cl | CH |
| 127 | O | $CO_2Me$ | H | H | CH | C—F | CH |
| 128 | O | $CO_2Me$ | H | H | CH | C—$NO_2$ | CH |
| 129 | O | $CO_2Me$ | H | H | CH | C—$CF_3$ | CH |
| 130 | O | $CO_2Me$ | H | H | CH | C—CN | CH |
| 131 | O | $CO_2Me$ | H | H | CH | C—$CO_2Me$ | CH |
| 132 | O | $CO_2Me$ | H | H | CH | C—$OCH_3$ | CH |
| 133 | O | $CO_2Me$ | H | H | CH | C—$OCF_3$ | CH |
| 134 | O | $CO_2Me$ | H | H | CH | C—Cl | C—Cl |
| 135 | O | $CO_2Me$ | H | H | C—F | C—Cl | C—Cl |
| 136 | O | $CO_2Me$ | H | H | C—$OCH_3$ | C—$OCH_3$ | CH |
| 137 | O | $CO_2Me$ | H | H | CH | C—F | C—Cl |
| 138 | O | $CO_2Me$ | Cl | H | C—Cl | CH | CH |
| 139 | O | H | H | H | CH | CH | N |
| 140 | O | H | H | H | CH | C—Cl | N |
| 141 | O | H | H | H | CH | C—$OCH_3$ | N |
| 142 | O | H | H | H | C—Cl | CH | N |
| 143 | O | H | H | H | CH | C—$CF_3$ | N |
| 144 | O | H | H | Cl | CH | C—$CF_3$ | N |
| 145 | O | Cl | H | H | CH | CH | N |
| 146 | O | Cl | H | H | CH | C—Cl | N |
| 147 | O | Cl | H | H | CH | C—$OCH_3$ | N |
| 148 | O | Cl | H | H | C—Cl | CH | N |
| 149 | O | Cl | H | H | CH | C—$CF_3$ | N |
| 150 | O | Cl | H | Cl | CH | C—$CF_3$ | N |
| 151 | O | H | H | H | N | C—Cl | CH |
| 152 | O | H | H | H | N | C—F | CH |
| 153 | O | H | H | H | N | C—$OCF_3$ | CH |
| 154 | O | H | H | H | N | C—$CF_3$ | CH |
| 155 | O | H | H | H | N | C—$OCH_3$ | CH |
| 156 | O | H | H | H | N | C—$OCH_2CF_3$ | CH |
| 157 | O | Cl | H | H | N | C—Cl | CH |
| 158 | O | Cl | H | H | N | C—F | CH |
| 159 | O | Cl | H | H | N | C—$OCF_3$ | CH |
| 160 | O | Cl | H | H | N | C—$CF_3$ | CH |
| 161 | O | Cl | H | H | N | C—$OCH_3$ | CH |
| 162 | O | Cl | H | H | N | C—$OCH_2CF_3$ | CH |
| 163 | O | H | H | H | CH | N | CH |
| 164 | O | Cl | H | H | CH | N | CH |
| 165 | $NCH_3$ | H | H | H | CH | C—$SCH_3$ | CH |
| 166 | $NCH_3$ | H | H | H | CH | C—$SO_2CH_3$ | CH |
| 167 | NH | H | H | H | CH | C—F | CH |
| 168 | NH | H | H | H | CH | C—$NO_2$ | CH |
| 169 | NH | H | H | H | CH | C—$CF_3$ | CH |
| 170 | NH | H | H | H | CH | C—CN | CH |
| 171 | NH | H | H | H | CH | C—Cl | CH |
| 172 | $NCH_3$ | H | H | H | CH | C—Br | CH |
| 173 | $NCH_3$ | $CH_3$ | H | H | CH | CH | CH |
| 174 | $NCH_3$ | H | H | H | CH | C—OPh | CH |
| 175 | $NCH_3$ | H | H | H | C—Cl | C—OPh-4-Cl | CH |
| 176 | $NCH_3$ | H | H | H | CH | C—OPh-4-Br | CH |
| 177 | NH | H | H | H | CH | C—$OCF_3$ | CH |
| 178 | NH | H | H | H | CH | C—Cl | C—Cl |
| 179 | $NCH_3$ | Cl | H | H | CH | C—Ph-4-Cl | CH |

TABLE 1-continued

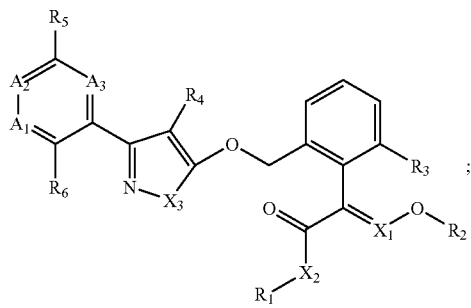

(I)

wherein: $R_1$, $R_2$ = $CH_3$, $R_3$ = H, $X_1$ = CH, $X_2$ = O

| No. | $X_3$ | $R_4$ | $R_5$ | $R_6$ | $A_1$ | $A_2$ | $A_3$ |
|-----|-------|-------|-------|-------|-------|-------|-------|
| 180 | NCH$_3$ | CH$_3$ | H | H | CH | C—C$_2$H$_5$ | CH |
| 181 | NH | Cl | H | H | CH | C—F | CH |
| 182 | NH | Cl | H | H | CH | C—NO$_2$ | CH |
| 183 | NH | Cl | H | H | CH | C—CF$_3$ | CH |
| 184 | NH | Cl | H | H | CH | C—CN | CH |
| 185 | NH | Cl | H | H | CH | C—CO$_2$Me | CH |
| 186 | NCH$_3$ | CH$_3$ | H | H | CH | C—OCH$_3$ | CH |
| 187 | NH | Cl | H | H | CH | C—OCF$_3$ | CH |
| 188 | NCH$_3$ | CH$_3$ | H | H | CH | C—CH$_3$ | CH |
| 189 | NCH$_3$ | H | H | Cl | C—H | C—H | C—H |
| 190 | NPri | H | H | H | CH | C—Cl | CH |
| 191 | NH | Cl | H | H | CH | C—F | C—Cl |
| 192 | NH | Cl | Cl | H | C—Cl | CH | CH |
| 193 | NCH3 | CN | H | H | CH | CH | CH |
| 194 | NH | CN | H | H | CH | C—Cl | CH |
| 195 | NH | CN | H | H | CH | C—F | CH |
| 196 | NH | CN | H | H | CH | C—NO$_2$ | CH |
| 197 | NH | CN | H | H | CH | C—CF$_3$ | CH |
| 198 | NH | CN | H | H | CH | C—CN | CH |
| 199 | NCH$_3$ | Ph-4-Cl | H | H | CH | C—Cl | CH |
| 200 | NCH$_3$ | OPh | H | H | CH | C—Cl | CH |
| 201 | NH | CN | H | H | CH | C—OCF$_3$ | CH |
| 202 | NH | CN | H | H | CH | C—Cl | C—Cl |
| 203 | NH | CN | H | H | C—F | C—Cl | C—Cl |
| 204 | NCH$_3$ | C$_2$H$_5$ | H | H | CH | C—Cl | CH |
| 205 | NCH$_3$ | C$_3$H$_7$-n | H | H | CH | C—Cl | CH |
| 206 | NCH$_3$ | C$_3$H$_7$-i | H | H | CH | C—Cl | CH |
| 207 | NCH$_3$ | Ph | H | H | CH | C—Cl | CH |
| 208 | NH | CO$_2$Me | H | H | CH | C—Cl | CH |
| 209 | NH | CO$_2$Me | H | H | CH | C—F | CH |
| 210 | NH | CO$_2$Me | H | H | CH | C—NO$_2$ | CH |
| 211 | NH | CO$_2$Me | H | H | CH | C—CF$_3$ | CH |
| 212 | NH | CO$_2$Me | H | H | CH | C—CN | CH |
| 213 | NH | CO$_2$Me | H | H | CH | C—CO$_2$Me | CH |
| 214 | NCH$_3$ | H | H | H | CH | CH | C—OCH$_3$ |
| 215 | NH | CO$_2$Me | H | H | CH | C—OCF$_3$ | CH |
| 216 | NH | CO$_2$Me | H | H | CH | C—Cl | C—Cl |
| 217 | NH | CO$_2$Me | H | H | C—F | C—Cl | C—Cl |
| 218 | NH | CO$_2$Me | H | H | C—OCH$_3$ | C-OCH$_3$ | CH |
| 219 | NH | CO$_2$Me | H | H | CH | C—F | C—Cl |
| 220 | NH | CO$_2$Me | Cl | H | C—Cl | CH | CH |
| 221 | NH | H | H | H | CH | CH | N |
| 222 | NH | H | H | H | CH | C—Cl | N |
| 223 | NH | H | H | H | CH | C—OCH$_3$ | N |
| 224 | NH | H | H | H | C—Cl | CH | N |
| 225 | NH | H | H | H | CH | C—CF$_3$ | N |
| 226 | NH | H | H | Cl | CH | C—CF$_3$ | N |
| 227 | NH | Cl | H | H | CH | CH | N |
| 228 | NH | Cl | H | H | CH | C—Cl | N |
| 229 | NH | Cl | H | H | CH | C—OCH$_3$ | N |
| 230 | NH | Cl | H | H | C—Cl | CH | N |
| 231 | NH | Cl | H | H | CH | C—CF$_3$ | N |
| 232 | NH | Cl | H | Cl | CH | C—CF$_3$ | N |
| 233 | NH | H | H | H | N | C—Cl | CH |
| 234 | NH | H | H | H | N | C—F | CH |
| 235 | NH | H | H | H | N | C—OCF$_3$ | CH |
| 236 | NH | H | H | H | N | C—CF$_3$ | CH |
| 237 | NH | H | H | H | N | C—OCH$_3$ | CH |
| 238 | NH | H | H | H | N | C—OCH$_2$CF$_3$ | CH |

TABLE 1-continued (I)

wherein: R₁, R₂ = CH₃, R₃ = H, X₁ = CH, X₂ = O

| No. | X₃ | R₄ | R₅ | R₆ | A₁ | A₂ | A₃ |
|-----|----|----|----|----|----|----|----|
| 239 | NH | Cl | H | H | N | C—Cl | CH |
| 240 | NH | Cl | H | H | N | C—F | CH |
| 241 | NH | Cl | H | H | N | C—OCF₃ | CH |
| 242 | NH | Cl | H | H | N | C—CF₃ | CH |
| 243 | NH | Cl | H | H | N | C—OCH₃ | CH |
| 244 | NH | Cl | H | H | N | C—OCH₂CF₃ | CH |
| 245 | NH | H | H | H | CH | N | CH |
| 246 | NH | Cl | H | H | CH | N | CH |

Physical and chemical property and ¹HNMR spectrum (¹HNMR, 300 Hz, internal standard:TMS, CDCl₃) of some compounds of this invention are as follows:

Compound 1: m.p. 123-127° C. δppm 7.73-7.21(m, 10H, Ar—H), 5.78(s, 1H, Het-H), 5.04(s, 2H, CH₂), 3.84(s, 3H, NCH₃), 3.71(s, 6H, 2OCH₃).

Compound 2: m.p. 129-121° C. δppm 7.61-7.16(m, 9H, Ar—H), 5.67(s, 1H, Het-H), 5.09(s, 2H, CH₂), 3.82(s, 3H, NCH₃), 3.71(s, 3H, OCH₃), 3.69(s, 3H, OCH₃).

Compound 3: m.p. 107-109° C. δppm 7.71-7.02(m, 9H, Ar—H), 5.73(s, 1H, Het-H), 5.04(s, 2H, CH₂), 3.84(s, 3H, NCH₃), 3.71(s, 6H, 2OCH₃).

Compound 4: m.p. 162-164° C. δppm 8.66-7.27(m, 8H, Ar—H), 5.85(s, 1H, Het-H), 5.06(s, 2H, CH₂), 3.85(s, 3H, NCH₃), 3.73(s, 3H, OCH₃), 3.72(s, 3H, OCH₃).

Compound 5: viscous oil. δppm 7.75-7.16(m, 9H, Ar—H), 5.73(s, 1H, Het-H), 5.11(s, 2H, CH₂), 3.82(s, 3H, NCH₃), 3.74(s, 3H, OCH₃), 3.69(s, 3H, OCH₃).

Compound 10: m.p. 154-157° C. δppm 3.70-3.72(6H, d), 3.83(3H, d), 5.05(2H, s), 6.00(1H, s), 7.19-7.22(1H, m), 7.25-7.28(1H, m), 7.36-7.39(2H, m), 7.42-7.43(1H, m), 7.51-7.54(1H, m), 7.61(1H, s), 7.71-7.74(1H, m).

Compound 11: δppm 3.67(3H, s), 3.83(3H, s), 4.06(3H, s), 5.00(2H, s), 5.27(1H, m), 7.15-7.18(1H, m), 7.23-7.27(2H, m), 7.33-7.43(1H, m), 7.58(1H, s), 7.76(1H, s), 7.90-7.93(1H, m).

Compound 12: viscous oil.

Compound 15: m.p. 137-139° C. δppm 2.35(3H, s), 3.70(3H, s), 3.71(3H, s), 3.84(3H, s), 5.03(2H, s), 5.75(1H, s), 7.16-7.18(1H, m), 7.36-7.39(2H, m), 7.51-7.55(1H, m), 7.59-7.62(3H, m).

Compound 29: m.p. 56-60° C. δppm (DMSO) 2.79(3H, s), 3.58(3H, s), 3.78(3H, s), 4.09(2H, s), 7.05(1H, m), 7.26-7.29(2H, m), 7.47-7.50(2H, m), 7.64-7.67(2H, m), 7.74-7.77(2H, m).

Compound 30: m.p. 69-71° C. δppm 1.85(3H, s), 3.61(3H, s), 3.69(3H, s), 3.82(3H, s), 5.16(2H, s), 7.15-7.19(1H, m), 7.23-7.26(2H, m), 7.31-7.40(2H, m), 7.43-7.46(2H, m), 7.58(1H, s), 7.61-7.65(1H, m).

Compound 69: m.p. 137-140° C. δppm 8.30-7.27(m, 8H, Ar—H), 5.79(s, 1H, Het-H), 5.06(s, 2H, CH₂), 3.85(s, 3H, NCH₃), 3.73(s, 3H, OCH₃), 3.72(s, 3H, OCH₃).

Compound 74: m.p. 92-94° C. δppm 3.68(3H, s), 3.71(3H, s), 3.83(3H, s), 4.32-4.40(2H, q), 5.03(2H, s), 5.71(1H, s), 6.91-6.96(2H, m), 7.19-7.22(1H, m), 7.34-7.41(2H, m), 7.52-7.55(1H, m), 7.61(1H, s), 7.64-7.69(2H, m).

Compound 80: m.p. 122-125° C. δppm 3.71-3.72(6H, d), 3.85(3H, s), 4.72-4.81(2H, m), 5.06(2H, s), 5.74(1H, s), 6.86-6.89(1H, d), 7.20-7.26(1H, m), 7.36-7.40(2H, m), 7.51-7.54(1H, m), 7.62(1H, s), 8.03-8.07(1H, dd), 8.42-8.43(1H, m).

Compound 83: viscous oil. δppm 7.78-7.15(m, 10H, Ar-H), 5.46(s, 1H, Het-H), 5.18(s, 2H, CH₂), 3.85(s, 3H, OCH₃), 3.72(s, 3H, OCH₃).

Compound 84: viscous oil.

Compound 86: m.p. 137-140° C. δppm 8.22-7.20(m, 9H, Ar—H), 5.54(s, 1H, Het-H), 5.21(s, 2H, CH₂), 3.86(s, 3H, OCH₃), 3.74(s, 3H, OCH₃).

Compound 97: viscous oil. δppm 2.38(3H, s), 3.72(3H, s), 3.85(3H, s), 5.17(2H, s), 5.43(1H, s), 7.21-7.26(3H, m), 7.37-7.40(2H, m), 7.59-7.64(4H, m).

Compound 111: viscous oil. δppm 1.91(3H, s), 3.70(3H, s), 3.83(3H, s), 5.31(2H, s), 7.31-7.35(1H, m), 7.37-7.44(4H, m), 7.55-7.61(4H, m).

Compound 151: viscous oil. δppm 3.73(3H, s), 3.86(3H, s), 5.20(2H, s), 5.48(1H, s), 7.26(1H, m), 7.37-7.42(3H, m), 7.55-7.58(1H, m), 7.64(1H, s), 8.02-8.06(1H, dd), 8.66-8.67(1H, d).

Compound 165: m.p. 127-129° C. δppm 2.50(3H, s), 3.69-3.71(6H, d), 3.83(3H, s), 5.03(2H, s), 5.74(1H, s), 7.19-7.23(2H, m), 7.26-7.27(1H, m), 7.36-7.39(2H, m), 7.52-7.56(1H, m), 7.61-7.62(2H, m), 7.65(1H, s).

Compound 172: m.p. 104-106° C. δppm 3.68-3.75(6H, m), 3.83(3H, s), 5.03(2H, s), 5.74(1H, s), 7.19-7.23(1H, mn), 7.36-7.39(2H, m), 7.46(1H, m), 7.48-7.49(1H, m), 7.52-7.55(1H, m), 7.56-7.57(1H, m), 7.59-7.60(1H, m), 7.61(1H, s).

Compound 173: viscous oil. δppm 1.87(3H, s), 3.63(3H, s), 3.69(3H, s), 3.82(3H, s), 5.16(2H, s), 7.16-7.19(1H, m), 7.30-7.49(7H, m), 7.59(1H, s), 7.64-7.67(1H, m).

Compound 174: viscous oil. δppm 3.69(3H, s), 3.71(3H, s), 3.84(3H, s), 5.03(2H, s), 5.73(1H, s), 6.99-7.03(2H, m), 7.10(2H, m), 7.19-7.22(1H, m), 7.31-7.34(2H, m), 7.36-7.39(2H, mn), 7.52-7.55(1H, mn), 7.61(1H, s), 7.66-7.69(2H, m).

Compound 179: m.p. 161-163° C. δppm 3.71(3H, s), 3.72(3H, s), 3.85(3H, s), 5.05(2H, s), 5.81(1H, s), 6.82-6.85(1H, m), 7.20-7.24(1H, m), 7.35-7.42(4H, m), 7.52-7.57(4H, m), 7.52-7.57(4H, m), 7.62(1H, s), 7.76-7.81(2H, m).

Compound 180: viscous oil. δppm 1.26-1.31(3H, m), 1.87(3H, s), 2.70(2H, q), 3.63-3.69(6H, d), 3.82(3H, s), 5.15(2H, s), 7.24-7.28(7H, m), 7.59(1H, s), 7.62-7.65(1H, d).

Compound 186: viscous oil. δppm 2.48(3H, s), 3.68-3.70(6H, d), 3.82(3H, s), 5.02(2H, s), 5.740(1H, s), 7.22-7.25(2H, m), 7.35-7.37(2H, m), 7.38-7.52(1H, m), 7.61-7.65(2H, m).

Compound 188: viscous oil. δppm 1.86(3H, s), 2.41(3H, s), 3.62(3H, s), 3.68(3H, s), 3.82(3H, s), 5.15(2H, s), 7.19-7.22(3H, m), 7.29-7.32(4H, m), 7.59(1H, s), 7.62-7.64(1H, s).

Compound 189: viscous oil. δppm 3.59(3H, s), 3.71(3H, s), 3.82(3H, s), 5.11(2H, s), 5.67(1H, s), 7.26-7.30(2H, d), 7.35(4H, s), 7.37-7.39(1H, m), 7.40-7.60(2H, m).

Compound 190: viscous oil. δppm 1.46-1.48(6H, d), 3.71(3H, s), 3.83(3H, s), 4.57(1H, m), 5.03(2H, s), 5.73(1H, s), 7.18-7.22(2H, m), 7.30-7.32(2H, d), 7.36-7.39(2H, m), 7.51(1H, m), 7.61(1H, s), 7.66-7.69(2H, m).

Compound 214: viscous oil. δppm 1.86(3H, s), 2.41(3H, s), 3.63-3.69(6H, d), 3.82(3H, s), 5.16(2H, s), 7.19-7.25(3H, m), 7.26-7.287(3H, m), 7.35-7.36(1H, m), 7.38-7.59(1H, m).

TABLE 2

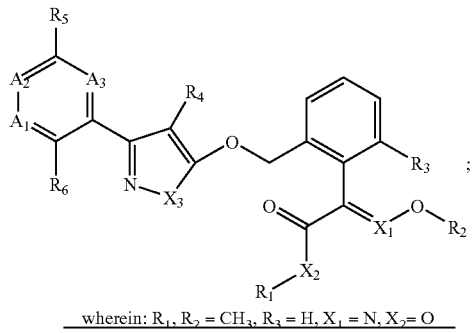

(I)

wherein: $R_1$, $R_2$ = $CH_3$, $R_3$ = H, $X_1$ = N, $X_2$ = O

| No. | $X_3$ | $R_4$ | $R_5$ | $R_6$ | $A_1$ | $A_2$ | $A_3$ |
|---|---|---|---|---|---|---|---|
| 247 | $NCH_3$ | H | H | H | CH | CH | CH |
| 248 | $NCH_3$ | H | H | H | CH | C—Cl | CH |
| 249 | $NCH_3$ | H | H | H | CH | C—F | CH |
| 250 | $NCH_3$ | H | H | H | CH | C—$NO_2$ | CH |
| 251 | $NCH_3$ | H | H | H | CH | C—$CF_3$ | CH |
| 252 | $NCH_3$ | H | H | H | CH | C—CN | CH |
| 253 | $NCH_3$ | H | H | H | CH | C—$CO_2$Me | CH |
| 254 | $NCH_3$ | H | H | H | CH | C—$SCH_3$ | CH |
| 255 | $NCH_3$ | H | H | H | CH | C—$OCF_3$ | CH |
| 256 | $NCH_3$ | H | H | H | CH | C—Cl | C—Cl |
| 257 | NPri | H | H | H | CH | C—Cl | C—H |
| 258 | $NCH_3$ | H | H | H | C—$OCH_3$ | C—$OCH_3$ | CH |
| 259 | $NCH_3$ | H | H | H | CH | C—F | C—Cl |
| 260 | $NCH_3$ | H | Cl | H | C—Cl | CH | CH |
| 261 | $NCH_3$ | H | H | H | CH | C—Br | CH |
| 262 | $NCH_3$ | Cl | H | H | CH | C—Cl | CH |
| 263 | $NCH_3$ | Cl | H | H | CH | C—F | CH |
| 264 | $NCH_3$ | Cl | H | H | CH | C—$NO_2$ | CH |
| 265 | $NCH_3$ | Cl | H | H | CH | C—$CF_3$ | CH |
| 266 | $NCH_3$ | Cl | H | H | CH | C—CN | CH |
| 267 | $NCH_3$ | Cl | H | H | CH | C—$CO_2$Me | CH |
| 268 | $NCH_3$ | H | H | H | CH | C—$CH_3$ | CH |
| 269 | $NCH_3$ | Cl | H | H | CH | C—$OCF_3$ | CH |
| 270 | $NCH_3$ | Cl | H | H | CH | C—Cl | C—Cl |

TABLE 2-continued

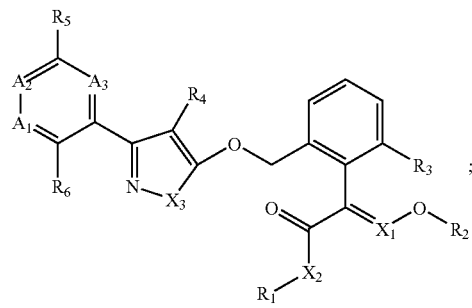

(I)

wherein: $R_1$, $R_2$ = $CH_3$, $R_3$ = H, $X_1$ = N, $X_2$ = O

| No. | $X_3$ | $R_4$ | $R_5$ | $R_6$ | $A_1$ | $A_2$ | $A_3$ |
|---|---|---|---|---|---|---|---|
| 271 | $NCH_3$ | Cl | H | H | C—F | C—Cl | C—Cl |
| 272 | $NCH_3$ | Cl | H | H | C—$OCH_3$ | C—$OCH_3$ | CH |
| 273 | $NCH_3$ | Cl | H | H | CH | C—F | C—Cl |
| 274 | $NCH_3$ | Cl | Cl | H | C—Cl | CH | CH |
| 275 | $NCH_3$ | H | H | H | CH | CH | N |
| 276 | $NCH_3$ | H | H | H | CH | C—Cl | N |
| 277 | $NCH_3$ | H | H | H | CH | C—$OCH_3$ | N |
| 278 | $NCH_3$ | H | H | H | C—Cl | CH | N |
| 279 | $NCH_3$ | H | H | H | CH | C—$CF_3$ | N |
| 280 | $NCH_3$ | H | H | Cl | CH | C—$CF_3$ | N |
| 281 | $NCH_3$ | Cl | H | H | CH | CH | N |
| 282 | $NCH_3$ | Cl | H | H | CH | C—Cl | N |
| 283 | $NCH_3$ | Cl | H | H | CH | C—$OCH_3$ | N |
| 284 | $NCH_3$ | H | H | H | CH | C—Br | N |
| 285 | $NCH_3$ | Cl | H | H | CH | C—$CF_3$ | N |
| 286 | $NCH_3$ | Cl | H | Cl | CH | C—$CF_3$ | N |
| 287 | $NCH_3$ | H | H | H | N | C—Cl | CH |
| 288 | $NCH_3$ | H | H | H | N | C—F | CH |
| 289 | $NCH_3$ | H | H | H | N | C—$OCF_3$ | CH |
| 290 | $NCH_3$ | H | H | H | N | C—$CF_3$ | CH |
| 291 | $NCH_3$ | H | H | H | N | C—$OCH_3$ | CH |
| 292 | $NCH_3$ | H | H | H | N | C—$OCH_2CF_3$ | CH |
| 293 | $NCH_3$ | Cl | H | H | N | C—Cl | CH |
| 294 | $NCH_3$ | Cl | H | H | N | C—F | CH |
| 295 | $NCH_3$ | Cl | H | H | N | C—$OCF_3$ | CH |
| 296 | $NCH_3$ | Cl | H | H | N | C—$CF_3$ | CH |
| 297 | $NCH_3$ | Cl | H | H | N | C—$OCH_3$ | CH |
| 298 | $NCH_3$ | Cl | H | H | N | C—$OCH_2CF_3$ | CH |
| 299 | $NCH_3$ | H | H | H | CH | N | CH |
| 300 | $NCH_3$ | Cl | H | H | CH | N | CH |
| 301 | O | H | H | H | CH | C—Cl | CH |
| 302 | O | $CH_3$ | H | H | CH | C—Cl | CH |
| 303 | O | H | H | H | CH | C—F | CH |
| 304 | O | H | H | H | CH | C—$NO_2$ | CH |
| 305 | O | H | H | H | CH | C—$CF_3$ | CH |
| 306 | O | H | H | H | CH | C—CN | CH |
| 307 | O | H | H | H | CH | C—$CO_2$Me | CH |
| 308 | O | H | H | H | CH | C—$OCH_3$ | CH |
| 309 | O | H | H | H | CH | C—$OCF_3$ | CH |
| 310 | O | H | H | H | CH | C—Cl | C—Cl |
| 311 | O | H | H | H | C—F | C—Cl | C—Cl |
| 312 | O | H | H | H | C—$OCH_3$ | C—$OCH_3$ | CH |
| 313 | O | H | H | H | CH | C—F | C—Cl |
| 314 | O | H | Cl | H | C—Cl | CH | CH |
| 315 | O | H | H | H | CH | C—$CH_3$ | CH |
| 316 | O | Cl | H | H | CH | C—Cl | CH |
| 317 | O | Cl | H | H | CH | C—F | CH |
| 318 | O | Cl | H | H | CH | C—$NO_2$ | CH |
| 319 | O | Cl | H | H | CH | C—$CF_3$ | CH |
| 320 | O | Cl | H | H | CH | C—CN | CH |
| 321 | O | Cl | H | H | CH | C—$CO_2$Me | CH |
| 322 | O | Cl | H | H | CH | C—$OCH_3$ | CH |
| 323 | O | Cl | H | H | CH | C—$OCF_3$ | CH |
| 324 | O | Cl | H | H | CH | C—Cl | C—Cl |
| 325 | O | Cl | H | H | C—F | C—Cl | C—Cl |
| 326 | O | Cl | H | H | C—$OCH_3$ | C—$OCH_3$ | CH |
| 327 | O | Cl | H | H | CH | C—F | C—Cl |
| 328 | O | Cl | Cl | H | C—Cl | CH | CH |
| 329 | O | H | H | H | CH | CH | N |

TABLE 2-continued (I)

wherein: $R_1, R_2 = CH_3, R_3 = H, X_1 = N, X_2 = O$

| No. | $X_3$ | $R_4$ | $R_5$ | $R_6$ | $A_1$ | $A_2$ | $A_3$ |
|---|---|---|---|---|---|---|---|
| 330 | O | H | H | H | CH | C—Cl | N |
| 331 | O | H | H | H | CH | C—OCH$_3$ | N |
| 332 | O | H | H | H | C—Cl | CH | N |
| 333 | O | H | H | H | CH | C—CF$_3$ | N |
| 334 | O | H | H | Cl | CH | C—CF$_3$ | N |
| 335 | O | Cl | H | H | CH | CH | N |
| 336 | O | Cl | H | H | CH | C—Cl | N |
| 337 | O | Cl | H | H | CH | C—OCH$_3$ | N |
| 338 | O | Cl | H | H | C—Cl | CH | N |
| 339 | O | Cl | H | H | CH | C—CF$_3$ | N |
| 340 | O | Cl | H | Cl | CH | C—CF$_3$ | N |
| 341 | O | H | H | H | N | C—Cl | CH |
| 342 | O | H | H | H | N | C—F | CH |
| 343 | O | H | H | H | N | C—OCF$_3$ | CH |
| 344 | O | H | H | H | N | C—CF$_3$ | CH |
| 345 | O | H | H | H | N | C—OCH$_3$ | CH |
| 346 | O | H | H | H | N | C—OCH$_2$CF$_3$ | CH |
| 347 | O | Cl | H | H | N | C—Cl | CH |
| 348 | O | Cl | H | H | N | C—F | CH |
| 349 | O | Cl | H | H | N | C—OCF$_3$ | CH |
| 350 | O | Cl | H | H | N | C—CF$_3$ | CH |
| 351 | O | Cl | H | H | N | C—OCH$_3$ | CH |
| 352 | O | Cl | H | H | N | C—OCH$_2$CF$_3$ | CH |
| 353 | O | H | H | H | CH | N | CH |
| 354 | O | Cl | H | H | CH | N | CH |

Physical and chemical property and $^1$HNMR spectrum ($^1$HNMR, 300 Hz, internal standard:TMS, CDCl$_3$) of some compounds of this invention are as follows:

Compound 247: viscous oil. δppm 3.69(3H, s), 3.85(3H, s), 4.06(3H, s), 5.02(2H, s), 5.79(1H, s), 7.23-7.26(1H, m), 7.27-7.30(1H, m), 7.34-7.39(2H, m), 7.44-7.53(3H, m), 7.70-7.73(2H, m).

Compound 248: m.p. 102-105° C. δppm 3.68(3H, s), 3.85(3H, s), 4.05(3H, s), 5.02(2H, s), 5.75(1H, s), 7.22-7.26(1H, m), 7.31-7.34(2H, m), 7.42-7.56(3H, m), 7.63-7.66(2H, m).

Compound 250: m.p. 138-140° C. δppm 3.72(3H, s), 3.86(3H, s), 4.06(3H, s), 5.04(2H, s), 5.81(1H, s), 7.26(1H, m), 7.48-7.53(3H, m), 7.85-7.88(2H, d), 8.21-8.24(2H, d).

Compound 254: m.p. 126-128° C. δppm 2.48-2.51(3H, m), 3.23(3H, s), 3.76(3H, s), 3.97(3H, s), 4.99(2H, s), 6.00(1H, s), 7.19-7.22(3H, m), 7.42-7.46(2H, m), 7.59-7.62(3H, m).

Compound 256: m.p. 177-179° C. δppm 3.77(3H, s), 3.87(3H, s), 4.05(3H, s), 5.07(2H, s), 6.07(1H, s), 7.26(1H, m), 7.27-7.29(1H, m), 7.44-7.48(4H, m), 7.77-7.82(1H, m).

Compound 257: viscous oil. δppm 1.45-1.48(6H, d), 3.85(3H, s), 4.06(3H, s), 4.53(1H, m), 5.00(2H, s), 5.75(1H, s), 7.22-7.26(1H, m), 7.30-7.33(2H, m), 7.43-7.49(3H, m), 7.53(1H, m), 7.65-7.69(2H, m).

Compound 261: viscous oil. δppm 3.64(3H, s), 3.88(3H, s), 4.06(3H, s), 5.01(2H, s), 5.75(1H, s), 7.25-7.26(2H, m), 7.45-7.60(6H, m).

Compound 268: m.p. 98-100° C. δppm 2.35(3H, s), 3.67(3H, s), 3.84(3H, s), 4.05(3H, s), 5.01(2H, s), 5.75(1H, s), 7.16-7.18(2H, m), 7.22-7.26(1H, m), 7.43-7.48(2H, m), 7.52-7.56(1H, m), 7.59-7.62(2H, m).

Compound 287: m.p. 142-143° C. δppm 3.68(3H, s), 3.86(3H, s), 4.05(3H, s), 5.02(2H, s), 5.78(1H, s), 7.26-7.33(1H, m), 7.46-7.49(4H, m), 7.99(1H, m), 8.66(1H, m).

Compound 292: m.p. 124-126° C. δppm 3.70(3H, s), 3.86(3H, s), 4.06(3H, s), 4.73-4.82(2H, m), 5.03(2H, s), 5.74(1H, s), 6.86-6.89(1H, d), 7.22-7.26(1H, m), 7.44-7.52(3H, m), 8.02-8.06(1H, m), 8.42-8.43(1H, m).

Compound 302: m.p. 99-101° C. δppm 1.89(3H, s), 3.88(3H, s), 4.06(3H, s), 5.27(2H, s), 7.26(1H, m), 7.41-7.48(4H, m), 7.56-7.59(3H, m).

Compound 315: m.p. 94-96° C. δppm 2.38(3H, s), 3.89(3H, s), 4.06(3H, s), 5.14(2H, s), 5.46(1H, s), 7.21-7.26(2H, m), 7.44-7.49(3H, m), 7.57-7.62(3H, m).

TABLE 3

(I)

wherein: $R_1, R_2 = CH_3, R_3 = H, X_1 = N, X_2 = NH$

| No. | $X_3$ | $R_4$ | $R_5$ | $R_6$ | $A_1$ | $A_2$ | $A_3$ |
|---|---|---|---|---|---|---|---|
| 355 | NCH$_3$ | H | H | H | CH | CH | CH |
| 356 | NCH$_3$ | H | H | H | CH | C—Cl | CH |
| 357 | NCH$_3$ | H | H | H | CH | C—F | CH |
| 358 | NCH$_3$ | H | H | H | CH | C—NO$_2$ | CH |
| 359 | NCH$_3$ | H | H | H | CH | C—CF$_3$ | CH |
| 360 | NCH$_3$ | H | H | H | CH | C—CN | CH |
| 361 | NCH$_3$ | H | H | H | CH | C—OCF$_3$ | CH |
| 362 | NCH$_3$ | H | H | H | CH | C—Cl | C—Cl |
| 363 | NCH$_3$ | H | H | H | C—F | C—Cl | C—Cl |
| 364 | NCH$_3$ | H | Cl | H | C—Cl | CH | CH |
| 365 | NCH$_3$ | H | H | H | CH | C—CH$_3$ | CH |
| 366 | NCH$_3$ | Cl | H | H | CH | C—Cl | CH |
| 367 | NCH$_3$ | Cl | H | H | CH | C—F | CH |
| 368 | NCH$_3$ | Cl | H | H | CH | C—NO$_2$ | CH |
| 369 | NCH$_3$ | Cl | H | H | CH | C—CF$_3$ | CH |
| 370 | NCH$_3$ | Cl | H | H | CH | C—CN | CH |
| 371 | NCH$_3$ | Cl | H | H | CH | C—OCF$_3$ | CH |
| 372 | NCH$_3$ | Cl | H | H | CH | C—Cl | C—Cl |
| 373 | NCH$_3$ | Cl | H | H | C—F | C—Cl | C—Cl |
| 374 | NCH$_3$ | Cl | Cl | H | C—Cl | CH | CH |
| 375 | O | H | H | H | CH | CH | CH |
| 376 | O | H | H | H | CH | C—Cl | CH |
| 377 | O | H | H | H | CH | C—F | CH |
| 378 | O | H | H | H | CH | C—NO$_2$ | CH |
| 379 | O | H | H | H | CH | C—CF$_3$ | CH |
| 380 | O | H | H | H | CH | C—CN | CH |
| 381 | O | H | H | H | CH | C—OCF$_3$ | CH |
| 382 | O | H | H | H | CH | C—Cl | C—Cl |
| 383 | O | H | H | H | C—F | C—Cl | C—Cl |
| 384 | O | H | Cl | H | C—Cl | CH | CH |
| 385 | O | CH$_3$ | H | H | CH | C—Cl | CH |
| 386 | O | H | H | H | CH | C—CH$_3$ | CH |
| 387 | O | Cl | H | H | CH | C—F | CH |
| 388 | O | Cl | H | H | CH | C—NO$_2$ | CH |
| 389 | O | Cl | H | H | CH | C—CF$_3$ | CH |
| 390 | O | Cl | H | H | CH | C—CN | CH |
| 391 | O | Cl | H | H | CH | C—OCF$_3$ | CH |
| 392 | O | Cl | H | H | CH | C—Cl | C—Cl |
| 393 | O | Cl | H | H | C—F | C—Cl | C—Cl |
| 394 | O | Cl | Cl | H | C—Cl | CH | CH |
| 395 | NCH$_3$ | H | H | H | CH | CH | N |

TABLE 3-continued

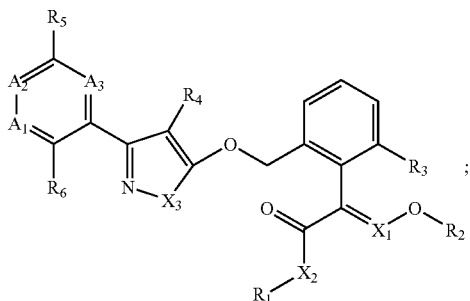

wherein: $R_1$, $R_2$ = $CH_3$, $R_3$ = H, $X_1$ = N, $X_2$ = NH

| No. | $X_3$ | $R_4$ | $R_5$ | $R_6$ | $A_1$ | $A_2$ | $A_3$ |
|---|---|---|---|---|---|---|---|
| 396 | $NCH_3$ | H | H | H | CH | C—Cl | N |
| 397 | $NCH_3$ | H | H | H | CH | C—$CF_3$ | N |
| 398 | $NCH_3$ | H | H | Cl | CH | C—$CF_3$ | N |
| 399 | $NCH_3$ | Cl | H | H | CH | CH | N |
| 400 | $NCH_3$ | Cl | H | H | CH | C—Cl | N |
| 401 | $NCH_3$ | Cl | H | H | CH | C—$CF_3$ | N |
| 402 | $NCH_3$ | Cl | H | Cl | CH | C—$CF_3$ | N |
| 403 | $NCH_3$ | H | H | H | N | C—Cl | CH |
| 404 | $NCH_3$ | H | H | H | N | C—F | CH |
| 405 | $NCH_3$ | H | H | H | N | C—$OCF_3$ | CH |
| 406 | $NCH_3$ | H | H | H | N | C—$CF_3$ | CH |
| 407 | $NCH_3$ | H | H | H | N | C—$OCH_2CF_3$ | CH |
| 408 | $NCH_3$ | Cl | H | H | N | C—Cl | CH |
| 409 | $NCH_3$ | Cl | H | H | N | C—F | CH |
| 410 | $NCH_3$ | Cl | H | H | N | C—$OCF_3$ | CH |
| 411 | $NCH_3$ | Cl | H | H | N | C—$CF_3$ | CH |
| 412 | $NCH_3$ | Cl | H | H | N | C—$OCH_2CF_3$ | CH |
| 413 | $NCH_3$ | H | H | H | CH | N | CH |
| 414 | $NCH_3$ | Cl | H | H | CH | N | CH |
| 415 | O | H | H | H | CH | CH | N |
| 416 | O | H | H | H | CH | C—Cl | N |
| 417 | O | H | H | H | CH | C—$CF_3$ | N |
| 418 | O | H | H | Cl | CH | C—$CF_3$ | N |
| 419 | O | Cl | H | H | CH | CH | N |
| 420 | O | Cl | H | H | CH | C—Cl | N |
| 421 | O | Cl | H | H | CH | C—$CF_3$ | N |
| 422 | O | Cl | H | Cl | CH | C—$CF_3$ | N |
| 423 | O | H | H | H | N | C—Cl | CH |
| 424 | O | H | H | H | N | C—F | CH |
| 425 | O | H | H | H | N | C—$OCF_3$ | CH |
| 426 | O | H | H | H | N | C—$CF_3$ | CH |
| 427 | O | H | H | H | N | C—$OCH_2CF_3$ | CH |
| 428 | O | Cl | H | H | N | C—Cl | CH |
| 429 | O | Cl | H | H | N | C—F | CH |
| 430 | O | Cl | H | H | N | C—$OCF_3$ | CH |
| 431 | O | Cl | H | H | N | C—$CF_3$ | CH |
| 432 | O | Cl | H | H | N | C—$OCH_2CF_3$ | CH |
| 433 | O | H | H | H | CH | N | CH |
| 434 | O | Cl | H | H | CH | N | CH |
| 435 | NPri | H | H | H | CH | C—Cl | CH |

Physical and chemical property and ¹HNMR spectrum (¹HNMR, 300Hz, internal standard:TMS, $CDCl_3$) of some compounds of this invention are as follows:

Compound 355: viscous oil. δppm 2.90-2.92(3H, d), 3.67 (3H, s), 3.96(3H, s), 5.02(2H, s), 5.82(1H, s), 6.80(1H, bs), 7.22-7.26(1H, m), 7.27-7.31(1H, m), 7.34-7.37(2H, m), 7.43-7.46(2H, m), 7.50-7.54(1H, m), 7.71-7.75(2H, m).

Compound 356: m.p. 133-135° C. δppm 2.92-2.93(3H, d), 3.74(3H, s), 3.96(3H, s), 5.05(2H, s), 5.86(1H, s), 6.81(1H, bs), 7.21-7.26(1H, m), 7.33-7.37(2H, m), 7.44-7.50(3H, m), 7.71-7.74(2H, m).

Compound 362: m.p. 106-108° C. δppm 2.91-2.93(3H, d), 3.49(3H, s), 3.97(3H, s), 5.21(2H, s), 6.07(1H, s), 6.83(1H, m), 7.26-7.34(2H, m), 7.44-7.50(5H, m).

Compound 365: m.p. 132-134° C. δppm 2.36(3H, s), 2.90-2.92(3H, d), 3.66(3H, s), 3.96(3H, s), 5.01(2H, s), 5.79(1H, s), 6.78(1H, bs), 7.16-7.26(3H, m), 7.43-7.50(3H, m), 7.61-7.64(2H, m).

Compound 385: m.p. 109-111° C. δppm 1.89(3H, s), 2.91-2.93(3H, d), 3.97(3H, s), 5.27(2H, s), 6.81(1H, bs), 7.26(1H, m), 7.41-7.46(4H, m), 7.57-7.60(3H, m).

Compound 386: m.p. 128-130° C. δppm 2.38(3H, s), 2.93-2.95(3H, d), 3.97(3H, s), 5.16(2H, s), 5.49(1H, s), 6.83(1H, bs), 7.21-7.26(3H, m), 7.43-7.46(2H, m), 7.54-7.57(1H, m), 7.61-7.63(2H, d).

Compound 407: m.p. 148-150° C. δppm 2.92-2.93(3H, d), 3.68(3H, s), 3.97(3H, s), 4.73-4.82(2H, m), 5.03(2H, s), 5.79 (1H, s), 6.82(1H, bs), 6.85-6.89(1H, d), 7.22-7.26(1H, m), 7.43-7.50(3H, m), 7.52-8.06(1H, m), 8.44-8.45(1H, m).

Compound 408: m.p. 140-142° C. δppm 2.92-2.93(3H, d), 3.67(3H, s), 3.97(3H, s), 5.02(2H, s), 5.82(1H, s), 6.82(1H, bs), 7.26-7.30(1H, m), 7.32-7.33(1H, m), 7.44-7.50(3H, m), 7.99(1H, m), 8.69(1H, m).

Compound 435: viscous oil. δppm 1.48-1.51(6H, d), 2.92-2.94(3H, m), 3.97(3H, s), 4.56(1H, m), 5.04(2H, s), 5.83(1H, s), 6.82(1H, bs), 7.21-7.26(1H, m), 7.29-7.35(2H, m), 7.43-7.52(3H, m), 7.74-7.76(2H, d).

The present invention also includes preparation of substituted azole compounds having formula I.

It can be prepared by reaction azoles compounds containing hydroxy group having general formula III with halomethylbenzene having general formula IV at the present of base:

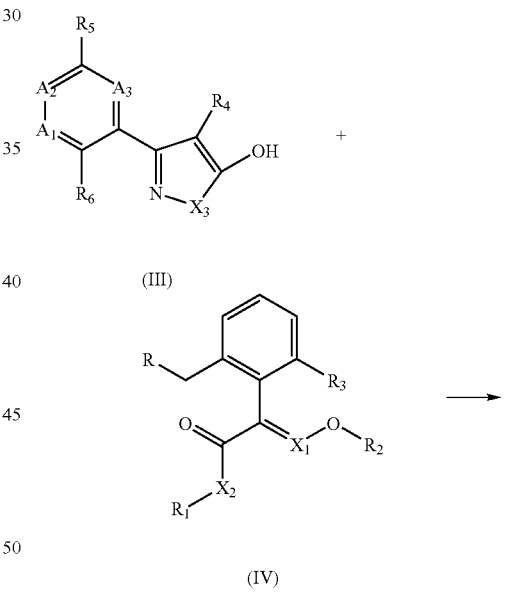

(III)

(IV)

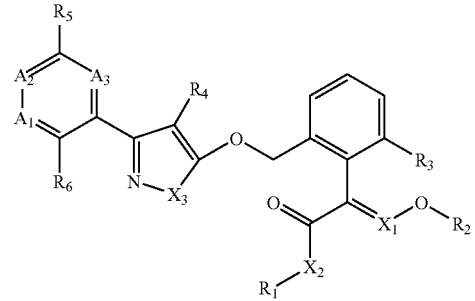

(I)

wherein: R is leaving group, such as Cl or Br. Other groups are as defined above.

The proper solvent mentioned may be selected from tetrahydrofuran, acetonitrile, toluene, xylene, benzene, DMF, DMSO, acetone or butanonie and so on.

The proper base mentioned may be selected from potassium hydroxide, sodium hydroxide, sodium carbonate, potassium carbonate, sodium bicarbonate, triethylamine, pyridine, sodium methoxide, sodium ethoxide, sodium hydride, potassium or sodium tert-butoxide and so on.

The proper temperature mentioned is from room temperature to boiling point of solvent. Normal temperature is from 20 to 100° C.

The reaction may be finished after 30 minutes-20 hours, generally 1-10 hours.

Compounds of the general formula (I) wherein $X_1$=N, $X_2$=NH can be prepared easily by reaction of compounds of the general formula (I) wherein $X_1$=N, $X_2$=O with methylamine.

Intermediate of the general formula (III) can be prepared by reaction of intermediate of the general formula (II) with (substituted)hydrazine or hydroxylanmine according to known methods. Intermediate of the general formula (II) can be bought or prepared according to known methods, refer to U.S. Pat. No. 3,781,438, CN1257490A, WO 9615115 and so on.

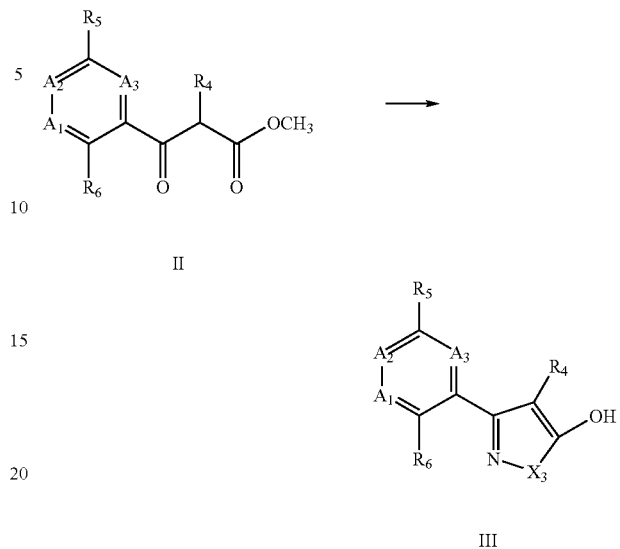

Some of the intermediates having general formula (III) are showed in table 4. The intermediates having general formula (IV) can be prepared according to known methods, refer to U.S. Pat. No. 4,723,034 and U.S. Pat. No. 5,554,578.

TABLE 4

| No. | $X_3$ | $R_4$ | $R_5$ | $R_6$ | $A_1$ | $A_2$ | $A_3$ | MP(° C.) |
|---|---|---|---|---|---|---|---|---|
| M1 | $NCH_3$ | H | H | H | C—H | C—Cl | C—H | 192-193 |
| M2 | $NCH_3$ | H | H | H | C—H | C—Cl | C—Cl | 214-217 |
| M3 | $NCH_3$ | H | H | H | C—H | C—Br | C—H | 195-198 |
| M4 | $NCH_3$ | H | H | H | C—H | C—F | C—H | 182-185 |
| M5 | $NCH_3$ | H | H | H | C—H | C—$OCH_2CF_3$ | C—H | 174-176 |
| M6 | $NCH_3$ | H | H | H | C—H | C—OPh | C—H | 176-178 |
| M7 | $NCH_3$ | H | H | H | C—H | C-Ph-4-Cl | C—H | |
| M8 | $NCH_3$ | H | H | H | C—H | C—$OCF_3$ | C—H | |
| M9 | $NCH_3$ | H | H | H | C—H | C—$CH_3$ | C—H | 183-185 |
| M10 | $NCH_3$ | $CH_3$ | H | H | C—H | C—$C_2H_5$ | C—H | 198-202 |
| M11 | $NCH_3$ | H | H | H | C—H | C—$NO_2$ | C—H | 254-256 |
| M12 | $NCH_3$ | H | H | H | C—H | C—$CF_3$ | C—H | |
| M13 | $NCH_3$ | H | H | H | C—F | C—Cl | C—Cl | |
| M14 | $NCH_3$ | H | H | H | C—H | C—$OCH_3$ | C—H | |
| M15 | $NCH_3$ | H | H | H | N | C—H | C—H | |
| M16 | $NCH_3$ | H | H | H | C—H | N | C—H | |
| M17 | $NCH_3$ | H | H | H | C—H | C—H | N | |
| M18 | $NCH_3$ | H | H | H | C—H | C—CN | C—H | |
| M19 | $NCH_3$ | H | H | H | C—H | C—$CO_2CH_3$ | C—H | |
| M20 | $NCH_3$ | H | H | H | C—H | C—$SCH_3$ | C—H | 178-180 |
| M21 | $NCH_3$ | H | H | H | C—H | C—$SO_2CH_3$ | C—H | |
| M22 | $NCH_3$ | H | H | H | C—$OCH_3$ | C—$OCH_3$ | C—H | |
| M23 | $NCH_3$ | H | H | H | C—F | C—Cl | C—H | |
| M24 | $NCH_3$ | H | H | H | C—Cl | C—F | C—H | |
| M25 | $NCH_3$ | H | Cl | H | C—Cl | C—H | C—H | |
| M26 | $NCH_3$ | H | $CF_3$ | H | C—$CF_3$ | C—H | C—H | |
| M27 | $NCH_3$ | H | Cl | H | C—Cl | C—$CH_3$ | C—H | |
| M28 | $NCH_3$ | H | Cl | H | C—Cl | C—Cl | C—H | |
| M29 | $NCH_3$ | H | H | $CH_3$ | C—H | C—$CH_3$ | C—$CH_3$ | |
| M30 | $NCH_3$ | H | H | Cl | C—H | C—Cl | C—Cl | |
| M31 | $NCH_3$ | H | H | Cl | C—H | C—H | C—Cl | |
| M32 | $NCH_3$ | H | Cl | H | C—H | C—Cl | C—Cl | |
| M33 | $NCH_3$ | H | Cl | H | C—H | C—Cl | C—H | |
| M34 | $NCH_3$ | $CH_3$ | H | H | C—H | C—Cl | C—H | 234-236 |
| M35 | $NCH_3$ | $C_2H_5$ | H | H | C—H | C—Cl | C—H | |
| M36 | $NCH_3$ | $C_3H_7$-i | H | H | C—H | C—Cl | C—H | |
| M37 | $NCH_3$ | $CH_3$ | H | H | C—H | C—$OCH_3$ | C—H | 198-200 |
| M38 | $NCH_3$ | Cl | H | H | C—H | C—Cl | C—H | 218-220 |
| M39 | $NCH_3$ | Br | H | H | C—H | C—Cl | C—H | |
| M40 | $NCH_3$ | CN | H | H | C—H | C—Cl | C—H | 124-128 |
| M41 | $NCH_3$ | $OCH_3$ | H | H | C—H | C—Cl | C—H | |

TABLE 4-continued

| No. | $X_3$ | $R_4$ | $R_5$ | $R_6$ | $A_1$ | $A_2$ | $A_3$ | MP(° C.) |
|---|---|---|---|---|---|---|---|---|
| M42 | $NCH_3$ | $CO_2CH_3$ | H | H | C—H | C—Cl | C—H | |
| M43 | $NCH_3$ | $CO_2C_2H_5$ | H | H | C—H | C—Cl | C—H | |
| M44 | $NCH_3$ | $CH_2CO_2C_2H_5$ | H | H | C—H | C—Cl | C—H | |
| M45 | $NCH_3$ | $CH_2CN$ | H | H | C—H | C—Cl | C—H | |
| M46 | $NC_2H_5$ | H | H | H | C—H | C—Cl | C—H | |
| M47 | $NC_2H_5$ | H | H | H | C—H | C—F | C—H | |
| M48 | $NC_2H_5$ | $CH_3$ | H | H | C—H | C—Cl | C—H | |
| M49 | $NC_3H_7$-i | H | H | H | C—H | C—Cl | C—H | 149-150 |
| M50 | $NC_3H_7$-i | H | H | H | C—H | C—F | C—H | |
| M51 | $NC_3H_7$-i | $CH_3$ | H | H | C—H | C—Cl | C—H | |
| M52 | $NCH_3$ | H | H | H | C—H | C—OPh-4-Cl | C—H | |
| M53 | $NCH_3$ | H | H | H | C—H | C—OPh-4-Br | C—H | |
| M54 | $NCH_3$ | H | H | H | N | C—Cl | C—H | 183-185 |
| M55 | $NCH_3$ | H | H | H | N | C—$OCH_2CF_3$ | C—H | 196-199 |
| M56 | $NCH_3$ | H | H | H | N | C—$OCH_3$ | C—H | |
| M57 | $NCH_3$ | H | H | H | N | C—$CF_3$ | C—H | |
| M58 | $NC_3H_7$-i | H | H | H | N | C—Cl | C—H | |
| M59 | $NCH_3$ | H | H | Cl | CH | C—$CF_3$ | N | |
| M60 | $NCH_3$ | H | H | Cl | CH | C—$CF_3$ | C—H | |
| M61 | O | H | H | H | C—H | C—Cl | C—H | 238-240 |
| M62 | O | H | H | H | C—H | C—Cl | C—Cl | |
| M63 | O | H | H | H | C—H | C—Br | C—H | |
| M64 | O | H | H | H | C—H | C—F | C—H | |
| M65 | O | H | H | H | C—H | C—$OCH_2CF_3$ | C—H | |
| M66 | O | H | H | H | C—H | C—OPh | C—H | |
| M67 | O | H | H | H | C—H | C-Ph-4-Cl | C—H | |
| M68 | O | H | H | H | C—H | C—$OCF_3$ | C—H | |
| M69 | O | H | H | H | C—H | C—$CH_3$ | C—H | 120-122 |
| M70 | O | H | H | H | C—H | C—$C_2H_5$ | C—H | |
| M71 | O | H | H | H | C—H | C—$NO_2$ | C—H | 178-180 |
| M72 | O | H | H | H | C—H | C—$CF_3$ | C—H | |
| M73 | O | $CH_3$ | H | H | C—H | C—Cl | C—H | 188-191 |
| M74 | O | $C_2H_5$ | H | H | C—H | C—Cl | C—H | |
| M75 | O | $C_3H_7$-i | H | H | C—H | C—Cl | C—H | |
| M76 | O | Cl | H | H | C—H | C—Cl | C—H | |
| M77 | O | Br | H | H | C—H | C—Cl | C—H | |
| M78 | O | CN | H | H | C—H | C—Cl | C—H | |
| M79 | O | $CO_2CH_3$ | H | H | C—H | C—Cl | C—H | |
| M80 | O | $CO_2C_2H_5$ | H | H | C—H | C—Cl | C—H | |
| M81 | O | $CH_2CO_2C_2H_5$ | H | H | C—H | C—Cl | C—H | |
| M82 | O | $CH_2CN$ | H | H | C—H | C—Cl | C—H | |
| M83 | O | H | H | H | N | C—Cl | C—H | >300 |
| M84 | $NCH_3$ | $CH_3$ | H | H | CH | CH | CH | 194-197 |
| M85 | $NCH_3$ | H | Cl | H | CH | CH | CH | |
| M86 | $NCH_3$ | $CH_3$ | H | H | CH | C—$CH_3$ | CH | 232-235 |
| M87 | O | H | H | H | CH | CH | CH | 124-126 |
| M88 | $NCH_3$ | H | H | Cl | CH | CH | CH | 261-263 |
| M89 | $NCH_3$ | H | H | H | CH | CH | C—$OCH_3$ | 148-150 |
| M90 | $NCH_3$ | H | OMe | H | C—$OCH_3$ | C—$OCH_3$ | CH | |
| M91 | $NCH_3$ | $C_3H_7$-n | H | H | C—H | C—Cl | C—H | |
| M92 | $NCH_3$ | $C_4H_9$-n | H | H | C—H | C—Cl | C—H | |
| M93 | $NCH_3$ | OPh | H | H | C—H | C—Cl | C—H | |
| M94 | $NCH_3$ | OPh-4-Cl | H | H | C—H | C—Cl | C—H | |
| M95 | $NCH_3$ | Ph | H | H | C—H | C—Cl | C—H | |
| M96 | $NCH_3$ | Ph-4-Cl | H | H | C—H | C—Cl | C—H | |

Physical and chemical property and $^1$HNMR spectrum ($^1$HNMR, 300 Hz, internal standard:TMS, $CDCl_3$) of some intermediates of this invention are as follows:

M1: δppm 3.57(3H, s), 5.69(1H, s), 7.29-7.32(2H, d), 7.64-7.67(2H, d).

M3: δppm 3.54(3H, s), 5.62(1H, s), 7.44-7.47(2H, d), 7.57-7.60(2H, d).

M4: δppm 3.55(3H, s), 5.62(1H, s), 7.10-7.16(2H, d), 7.67-7.72(2H, d).

M5: δppm 3.55(3H, s), 4.58-4.67(2H, q), 5.64(1H, s), 6.97-7.00(2H, d), 7.60-7.63(2H, d).

M6: δppm 3.58(3H, s), 5.62(1H, s), 6.93-6.99(3H, m), 7.05-7.10(2H, m), 7.31-7.36(2H, m), 7.62-7.65(2H, m).

M9: δppm 2.33(3H, s), 3.56(3H, s), 5.61(1H, s), 7.07-7.11(2H, d), 7.50-7.53(2H, d).

M10: δppm 1.24-1.29(3H, t), 1.78(3H, s), 2.66-2.69(2H, m), 3.50(3H, s), 7.21-7.23(2H, d), 7.27-7.30(2H, d).

M11: δppm 3.60(3H, s), 5.89(1H, s), 7.90-7.92(2H, d), 8.16-8.19(2H, d).

M12: δppm 3.52(3H, s), 5.85(1H, s), 7.39(4H, s).

M20: δppm 2.49(3H, s), 3.57(3H, s), 5.66(1H, s), 7.44-7.47(2H, d), 7.57-7.60(2H, d).

M34: δppm 1.78(3H, s), 3.50(3H, s), 7.33-7.36(2H, d), 7.47-7.50(2H, d), 9.42(1H, bs).

M37: δppm 1.91(3H, s), 3.60(3H, s), 3.87(3H, s), 6.99-7.01(2H, d), 7.24-7.27(2H, d).

M49: δppm 1.38-1.40(6H, d), 4.44-4.48(1H, m), 5.66(1H, s), 7.28-7.31(2H, d), 7.66-7.68(2H, d), 10.66(1H, bs).

M55: δppm 3.56(3H, s), 4.84-4.93(2H, m), 5.71(1H, s), 6.88-6.91(1H, d), 8.01-8.05(1H, dd), 8.41-8.42(1H, m).

M69: δppm 2.39(3H, s), 5.53(1H, s), 7.27-7.30(2H, d), 7.56-7.60(2H, d).

M71: δppm 4.38(1H, s), 7.79-7.82(2H, d), 8.16-8.19(2H, d).

M83: δppm 4.62(1H, s), 7.47-7.50(1H, d), 7.99-8.02(1H, d), 8.59(1H, d).

M84: δppm 1.79(3H, s), 3.51(3H, s), 7.31-7.33(2H, d), 7.45-7.47(2H, d).

M86: δppm 1.77(3H, s), 2.38(3H, s), 3.49(3H, s), 7.19-7.22(2H, d), 7.26-7.29(2H, d).

M88: δppm 3.49(3H, s), 5.71(1H, s), 6.98-7.05(2H, m), 7.26-7.31(2H, m).

The present invention also provides a composition of insecticides and fungicides, the active ingredients of the composition are the compounds having general formula (1), wherein the active ingredients being present in a total amount of 0.1 to 99% by weight.

The present invention, further more provides preparation method of the said composition thereon. The compounds of general formula (I) and their carrier are mixed. The said composition may be a single component compound or mixture of compounds with several components.

The carrier in the invention accords to the requirements: it is easy to apply to the sites being to be treated for the carrier after it is confected with active component. For example, the sites could be plant, seed or soil convenient for store, transport or operation. The carrier could de solid or liquid, including the liquid which usually turns from gas condition under pressure. And the carriers which are used to confect insecticidal, bactericidal composition are applied.

Suitable solid carriers include natural and synthetic clays and silicates, for example diatomaceous earths, talcs, magnesium aluminium silicates, aluminium silicates(kaoling), montmorillonites and micas; calcium carbonate; calcium sulphate; ammonium sulphate; synthetic silicon oxides and synthetic calcium silicates or aluminium silicates; elements, for example carbon and sulphur; natural and synthetic resins, for example coumarone resins, polyvinyl chloride, and styrene polymers and copolymers; solid polychlorophenols; bitumen; waxes; beeswax or paraffinwax for instance.

Suitable liquid carriers include water, alcohols such as isopropanol or alcohol; ketones such as acetone, methyl ethyl ketone, methyl isopropy ketone or cyclohexanone; ethers; aromatics such as benzene, xylene, toluene; petroleum fractions such as kerosene or mineral oils, chlorinated aliphatic hydrocarbons such as carbon tetrachloride, tetrachloride ethylene and or trichloride ethylene. Mixtures of these different liquids generally are often suitable.

The compositions of insecticides and fungicides are often formulated and transported in a concentrated form which is subsequently diluted by the user before application. The presence of small amounts of surfactant facilitates this process of dilution. Thus preferably at least one carrier in a composition according to the invention is a surfactant. For example the composition may contain at least two carriers, at least one of which is a surfactant.

A surfactant may be an emulsifier, a dispersant or a wetting agent; it may be nonionic or ionic. Examples of suitable surfactant include the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycol, sorbic alcohol, sucrose or pentaerythritol and condensations of these with ethylene oxide and/or propylene oxide; condensation products of fatty alcohol or alkyl phenols such as p-octylphenol or p-octylcresol, with ethylene-oxide and/or propylene oxide; sulphates or sulphonates of these condensation products; alkaline metal salts or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as sodium dodecylbenzene sulphonate.

Examples of compositions and formulations according to the invention are wettable powder, dustable powder, granule, aqueous solution, emulsifiable concentrate, emulsion, suspension concentrate, aerosol composition and fumigant. Wettable powder usually contains 25, 50 or 75% weight(ab.w) of active ingredient and usually contain in addition to solid inert carrier, 3-10% w of a dispersant and, where necessary, 0-10% w of stabiliser(s) and/or other additives such as penetrants or stickers. Dustable powder are usually formulated as a dust concentrate having a similar composition to that of a wettable powder but a dispersant, and are diluted with further solid carrier to give a composition usually containing 0.5-10% weight of active ingredient. Granules are usually prepared to have a size between 10 and 100 BS mesh (1.676-0.152 mm), and may be manufactured by agglomeration or impregnation techniques. Generally, granules contain 0.5-75% w active ingredient and 0-10% weight of additives such as stabilisers, surfactants, slow release modifiers. Emulsifiable concentrates usually contain, in addition to a solvent and, when necessary, co-solvent, 1-50% weight/volume (w/v) active ingredient, 2-20% w/v emulsifiers and 0-20% w/v of other additives such as stabilisers, penetrants and corrosion inhibitors. Suspension concentrates are usually contain 10-75% w active ingredient, 0.5-15% w of dispersing agents, 0.1-10% w of other additives such as defoamers, corrosion inhibitors, stabilisers, penetrants and stickers.

Aqueous dispersant and emulsions, for example compositions obtained by diluting a wettable powder or a concentrate according to the invention with water, also lie within the scope of the invention. The said emulsions may be of the water-in-oil or of the oil-in-water type.

The composition to which one or more other fungicides are added has wider spectrum activity than single compound having general formula (I). In addition, other fungicides may have synergistic effect on the fungicidal activity of the compound having general formula (I). The compound having general formula (I) can also be used with other insecticides, or with another fungicide and other insecticides simultaneously.

The invention has the following advantages:

The compounds of present invention have wide spectrum fungicidal activity, and may be used to control diseases in all sorts of plants caused by oomycete, basidiomycete, ascomycete pathogens and deuteromycete, and it may also provide good control efficacy at very low dosage because of the high activity. These compounds have penetration activity and can be used as soil and foliar fungicides. They can provide satisfied control of cucumber downy mildew, cucumber grey mold, cucumber powdery mildew, tomato early blight, tomato late blight, phytophthora blight of pepper, grape downy mildew, grape white rot, apple ring rot, apple alternaria leaf spot, rice sheath blight, rice blast, wheat leaf rust, wheat leaf blotch, wheat powdery mildew, rapesclerotiniose, corn southern leaf blight.

The compounds of present invention have very good insecticidal and acaricidal activity, and may be used to control insects and mites, such as armyworm, diamond backmoth, aphids and culex mosquitoes. All these attributes are suitable for integrated insect management.

Therefore this invention also include the application of the azole compounds of the general formula (I) and their compositions to control diseases and insects in plants. The use of methods are known to the technical personnel in the same field.

DESCRIPTION OF THE INVENTION IN DETAIL

The following examples are illustrative of the present invention.

PREPARATION EXAMPLE

Example 1

The Preparation of Compound 2

2.12 g of ethyl 3-(4-chlorophenyl)-3-oxopropanoate was dissolved in methanol, the solution was heated to reflux. Slightly excessive methyl hydrazine was added to the solution dropwisely, 3 hr later, the reaction was traced by Thin-Layer Chromatography, and the solution was condensed, cooled, crystal obtained, and filtrated. The residue was washed with methanol, dried, 1.5 g crystal of 3-(4-chlorophenyl)-1-methyl-1H-pyrazol-5-ol was obtained.

1.04 g of the above crystal of 3-(4-chloroplenyil)-1-methyl-1H-pyrazol-5-ol was dissolved in 5 ml of DMF, and NaH (0.36 g) was added to the solution. then the solution was stirred for 30 min. 1.42 g of methyl (E)-2-[2-(bromomethly)phenyl]-3-methoxyacrylate was added, the mixture was heated to 40° C. 3 hr later, the reaction was traced by Thin-Layer Chromatography, and the reaction mixture was poured into 50 ml brine, extracted with 100 ml ethyl acetate 3 times. The combined organic extracts were dried, and concentrated, to obtain the crude product. This was subjected to silica gel column chromatography, using a 1:4(volume/volume) mixture of ethyl acetate and petroleum ether (boiling point range: 60-90° C.) as the eluting solution to obtain viscous oil 1.3 g of compound 2 (solidification after deposited).

Example 2

The Preparation of Compound 69

0.15 g of NaH was charged in a flask, washed with petroleum ether, DMF 5 ml and 0.5 g of 3-(6-chloropyridin-3-yl)-1-methyl-1H-pyrazol-5-ol (prepared according to CN1257490A). After stirred at room temperature for 2 min, 0.7 g of methyl (E)-2-[2-(bromomethly)phenyl]-3-methoxyacrylate was added, the reaction temperature was rised to 60° C. 2 hr later, the reaction was traced by Thin-Layer Chromatography, and the reaction mixture was poured into 50 ml brine, extracted with 100 ml ethyl acetate 3 times. The combined organic extracts were dried, and concentrated, to obtain the crude product. The crude product was purified through silica gel column and 0.2 g of slight yellow solid was obtained.

Example 3

The Preparation of Compound 86

According to method of U.S. Pat. No. 3,781,438, 2 g of ethyl 3-(4-nitrophenyl)-3-oxopropanoate was dissolved in methanol, slightly excessive hydroxylamine hydrochloride and equivalent amount of sodium hydroxide were added, the mixture was heated to reflux. 3 hr later, the reaction was traced by Thin-Layer Chromatography, water was added to the reaction mixture, extracted with ethyl acetate, dried and concentrated to obtain 3-(4-nitrophenyl)isoxazol-5-ol as solid.

1 g of the above crystal of 3-(4-nitrophenyl)isoxazol-5-ol was dissolved in DMF, and 0.4 g of NaH was added to the solution, then the solution was stirred for 30 min. 1.4 g of methyl (E)-2-[2-(bromomethly)phenyl]-3-methoxyacrylate was added, the mixture was heated to 50° C. 6 hr later, the reaction was traced by Thin-Layer Chromatography, and the reaction mixture was poured into 50 ml brine, extracted with 100 ml ethyl acetate 3 times. The combined organic extracts were dried, and concentrated, the crude product was purified through silica gel column to obtain 1.5 g compound as solid.

Example 4

The Preparation of Compound 179

The mixture was added 0.2 g of compound 172 (prepared according to example 1), 0.08 g of 4-chlorophlenylboronic acid 0.2 g of anhydrous potassium carbonate, and 0.01 g of tetrakis(phenyl)phosphine palladium acetate in 10 ml of toluene was heated to reflux for 18 hr, cooled down to room temperature and filtrated. The mother liquor was concentrated and purified through silica gel column to obtain 0.2 g compound as solid.

Example 5

The Preparation of Compound 248

The mixture of 3-(4-chlorophenyl)-1-methyl-1H-pyrazol-5-ol(1.0 g), methyl (E)-2-[2-(bromomethly)phenyl]-2-(methoxyimino)acetate(1.5 g), and anhydrous potassium carbonate(2.1 g) in DMF (15 ml) was stirred and reacted at 70-80° C. for 7 hr (the reaction was traced by Thin-Layer Chromatography), and then poured into 100 ml brine, extracted with 100 ml ethyl acetate 3 times. The combined organic extracts were dried, and concentrated. The crude product was purified through silica gel column to obtain 1.1 g compound 248 as solid.

Example 6

The Preparation of Compound 356

0.2 g of compound 248 was dissolved in 5 ml of THF, and slightly excessive methylamine solution (25-30%) was added dropwisely to the solution. The mixture was refluxed for 1 hr (the reaction was traced by Thin-Layer Chromatography), and then concentrated. Water was added to the residue, extracted with 10 ml ethyl acetate 3 times, the combined organic extracts were dried, and concentrated. The crude product was purified through silica gel column to obtain 0.16 g compound 356 as solid.

Other compounds were prepared according the above examples.

Formulation Example

Base on 100% Active Ingredient (weight/weight%)

Example 7

60% Wettable Powders

| | |
|---|---|
| Compound 69 | 60% |
| Sodium dodecylnaphthalenesulfate | 2% |
| Sodiumlignosulfonate | 9% |
| Kaolin | complement to 100% |

All the solid components are well mixed and shattered until the particle size reaches the standard (≦44 μm) in order to obtain 60% wettable powder.

Example 8

35% Emulsion Concentrate

| | |
|---|---|
| Compound 2 | 35% |
| Phosphorous acid | 10% |
| Ethylenoxy aliphatic acid glycerin ester | 15% |
| Cyclohexanone | complement to 100% |

Phosphorous acid is dissolved in cyclohexanone, then the compound 2 and ethylenoxy aliphatic acid glycerin ester are added, the emulsifiable in transparent solution, 35% emulsion concentrate, is obtained finally.

Example 9

30% Aqueous Suspension

| | |
|---|---|
| Compound 287 | 30% |
| Sodium dodecylnaphthalenesulfate | 4% |
| Hemicellulose | 2% |
| Epoxypropane | 8% |
| Water | complement to 100% |

The mixture of compound 287, 80% of the amount of water should being added and sodium dodecylnaphthalenesulfate are shattered in a mill (1 mm ball). Other components are dissolved in the rest water, and are added under stirring to obtain 30% aqueous suspension.

Example 10

25% Suspension Emulsifier

| | |
|---|---|
| Compound 12 | 25% |
| Alkylsulphonates (emulsifier 1) | 4% |
| Ethylenoxy aliphatic acid glycerin ester (emulsifier 2) | 2% |
| Calcium dodecylbenzenesulfate (emulsifier 3) | 1.5% |
| Polyethylenoxyalkyl propyl ether (dispersant) | 2.5% |
| Cyclohexanone (solvent 1) | 30% |
| Petroleum fractions (boiling point >200° C.) (solvent 2) | complement to 100% |

Compound 12 is dissolved in 80% of the amount of solvent should being added, and then emulsifiers and dispersant are added, the mixture is stirred completely and shattered in a mill (1 mm ball). Other solvents are added.

Biological Testing

Example 11

Determination of Fungicidal Activity

Determination of fungicidal activities against plant diseases of selected compounds were carried out by following procedure:

Technical samples were dissolved in DMF and diluted to required concentration wtih water containing 0.1% tween 80. Test solution was sprayed onto potted plant. Pathogen inoculation was carried out after 24 hours then plants were hold in growth chambers containing constant temperature and moisture for effect. When untreated plant was under desirable disease severity (after 1 week approximately), assessment were carried out by visual observation.

Part of the Test Results:

At 500 ppm, compound 1, 2, 4, 5, 11, 12, 30, 69, 74, 83, 84, 86, 165, 174, 179, 190, 248, 287, 356, 435 showed 100% control against wheat powdery mildew.

At 500 ppm, compound 1, 2, 4, 5, 11, 12, 30, 69, 74, 83, 84, 86, 190, 248, 287 showed 100% control against cucumber downy mildew.

At 500 ppm, compound 151, 247 showed 100% control against cucumber grey mold and wheat powdery mildew.

At 50 ppm, compound 1, 2, 4, 5, 30, 69, 84, 86, 287 showed 100% control against cucumber downy mildew and wheat powdery mildew.

At 100 ppm compound 2 showed more than 80% control against apple ring rot, wheat head blight, rape sclerotiniose, grape white rot, apple alternaria leaf spot, tomato early blight, tomato late blight, corn southern leaf blight and grape downy mildew.

Example 12

Determination of Insecticidal and Acaricidal Activity

Determination of insecticidal and acaricidal activities against plant diseases of selected compounds were carried out by following procedure:

Technical samples were dissolved in acetone and diluted to required concentration with water containing 0.1% of tween 80. Armyworm, diamondback moth and green peach aphid were treated with Potter spraying tower, and culex mosquito was treated with dipping culture method. Mortality investigation of test insects was carried out 2 to 3 days after treatment.

Part of test results:

At 150 ppm, compound 30 showed 100% control of armyworm, diamond backmoth, aphids and culex mosquitoes.

The invention claimed is:

1. A substituted azole compound of formula (I):

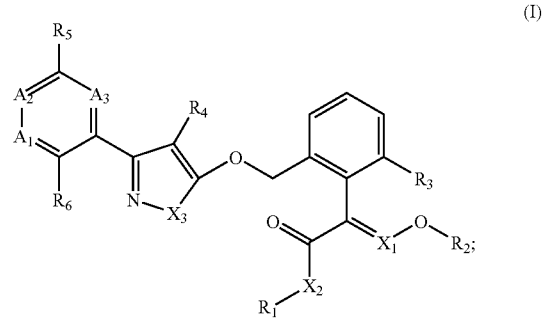

wherein
$X_1$ is CH;
$X_2$ is O;
$X_3$ is $NR_8$;
$A_1$ is $CR_9$;

$A_2$ is $CR_{10}$;

$A_3$ is $CR_{11}$;

$R_1$ and $R_2$ are $CH_3$;

$R_3$ is H;

$R_8$ is $C_1$-$C_6$alkyl;

$R_4$, $R_5$, $R_6$, $R_9$ and $R_{11}$ may be the same or different, selected from H, or $C_1$-$C_6$alkyl;

$R_{10}$ is a halogen;

and stereoisomer is E isomer.

2. The substituted azole compound according to the claim 1, wherein $R_8$ is $CH_3$.

3. A composition having as an active ingredient, a substituted azole compound of formula (I)

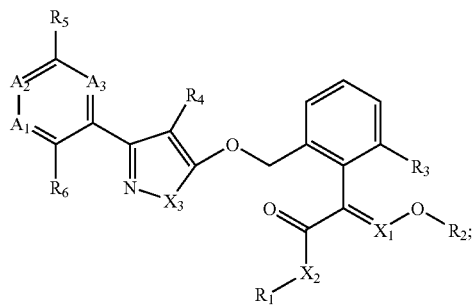

wherein $X_1$ is CH;

$X_2$ is O;

$X_3$ is $NR_8$;

$A_1$ is $CR_9$;

$A_2$ is $CR_{10}$;

$A_3$ is $CR_{11}$;

$R_1$ and $R_2$ are $CH_3$;

$R_3$ is H;

$R_8$ is $C_1$-$C_6$alkyl;

$R_4$, $R_5$, $R_6$, $R_9$, and $R_{11}$ may be the same or different, selected from H, or $C_1$-$C_6$alkyl;

$R_{10}$ is a halogen;

and stereoisomer is E isomer;

wherein the weight percentage of the active ingredient in the composition is from 0.1% to 99%.

4. A method for controlling fungi and insects in a plant which comprises administering the substituted azole compound of claim 1 to the plant.

5. The method according to claim 4, wherein the substituted azole compound is administered in the form of a composition.

6. (Previously presented, Withdrawn) The substitute azole compound according to claim 1, made by a method which comprises reacting an azole compound containing hydroxyl group having general formula (III) with a halomethylbenzene having general formula (IV) in the presence of a base:

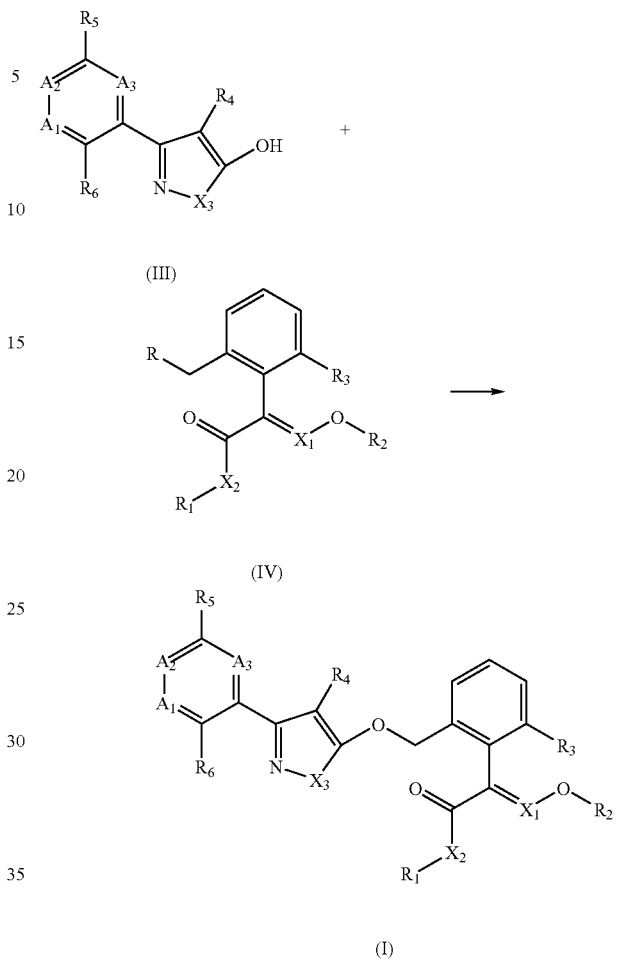

wherein: R is a leaving group.

7. The substitute azole compound according to claim 6, wherein the leaving group is Cl or Br.

8. The substituted azole compound according to the claim 1, wherein $R_4$ is H.

9. The substituted azole compound according to the claim 1, wherein $R_{10}$ is Cl, Br, or F.

10. A substituted azole compound of formula (I):

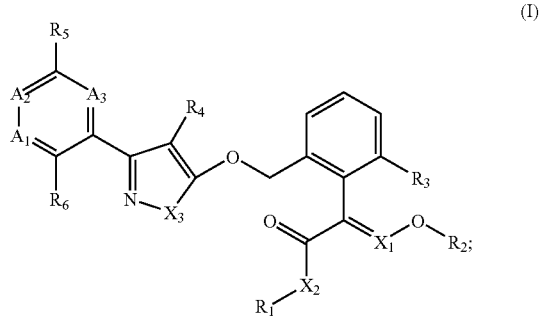

wherein
 $X_1$ is CH;
 $X_2$ is O;
 $X_3$ is $NR_8$;
 $A_1$ is $CR_9$;
 $A_2$ is $CR_{10}$;
 $A_3$ is $CR_{11}$;
 $R_1$ and $R_2$ are $CH_3$;
 $R_3$ and $R_4$ are H;
 $R_8$ is $CH_3$;
 $R_5$, $R_6$, $R_9$ and $R_{11}$ are H;
 $R_{10}$ is Cl;
 and stereoisomer is E isomer.

11. A composition having as an active ingredient, the substituted azole compound according to claim 10, wherein the weight percentage of the active ingredient in the composition is from 0.1% to 99%.

12. A method for controlling fungi and insects in a plant which comprises administering the substituted azole compound of claim 10 to the plant.

13. The method according to claim 12, wherein the substituted azole compound is administered in the form of a composition.

* * * * *